(12) United States Patent
Murata et al.

(10) Patent No.: US 9,790,508 B2
(45) Date of Patent: Oct. 17, 2017

(54) PEANUT-BINDING NUCLEIC ACID MOLECULE AND USE THEREOF

(71) Applicant: NEC Solution Innovators, Ltd., Tokyo (JP)

(72) Inventors: Tomoko Murata, Tokyo (JP); Katsunori Horii, Tokyo (JP); Ikuo Shiratori, Tokyo (JP); Jou Akitomi, Tokyo (JP); Naoto Kaneko, Tokyo (JP); Iwao Waga, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 0 days.

(21) Appl. No.: 15/100,833

(22) PCT Filed: Jun. 26, 2014

(86) PCT No.: PCT/JP2014/067022
§ 371 (c)(1),
(2) Date: Jun. 1, 2016

(87) PCT Pub. No.: WO2015/083391
PCT Pub. Date: Jun. 11, 2015

(65) Prior Publication Data
US 2016/0298117 A1    Oct. 13, 2016

(30) Foreign Application Priority Data
Dec. 4, 2013  (JP) ................................ 2013-251477

(51) Int. Cl.
C12N 15/115 (2010.01)
C12Q 1/68 (2006.01)

(52) U.S. Cl.
CPC .......... *C12N 15/115* (2013.01); *C12Q 1/6895* (2013.01); *C12N 2310/16* (2013.01)

(58) Field of Classification Search
None
See application file for complete search history.

(56) References Cited

U.S. PATENT DOCUMENTS

| | | | | |
|---|---|---|---|---|
| 5,605,662 A * | 2/1997 | Heller | ............... | B01J 19/0046 204/600 |
| 7,943,334 B2 | 5/2011 | Akimoto et al. | | |
| 7,947,447 B2 * | 5/2011 | Zichi | ............... | C12Q 1/6811 435/6.12 |
| 2006/0200878 A1 * | 9/2006 | Lutfiyya | ............ | C12N 15/8216 800/285 |
| 2007/0275427 A1 | 11/2007 | Akimoto et al. | | |
| 2012/0202195 A1 * | 8/2012 | Waga | ............... | C12Q 1/6825 435/6.1 |
| 2015/0056720 A1 | 2/2015 | Horii et al. | | |
| 2015/0086980 A1 | 3/2015 | Horii et al. | | |
| 2015/0086992 A1 | 3/2015 | Nitta | | |

FOREIGN PATENT DOCUMENTS

| | | |
|---|---|---|
| EP | 1 731 907 A1 | 12/2006 |
| JP | 2009-271091 A | 11/2009 |
| JP | 2013-233126 A | 11/2013 |
| WO | WO-2013/140681 A1 | 9/2013 |
| WO | WO-2013/141291 A1 | 9/2013 |

OTHER PUBLICATIONS

International Search Report corresponding to PCT/JP2014/067022, dated Sep. 22, 2014 (8 pages).
zh73d02.r1 Soares_fetal_liver_spleen_1NFLS_S1 *Homo sapiens* cDNA clone Image:471699 5-, mRNA sequence, [Jan. 28, 2011] (online); [retrieved on Sep. 10, 2014]; GenBank Accession No. W89056; <URL: http://www.ncbi.nlm.nih/gov/nucest/w89056> (2 pages).
ze76d05.s1 Soares_fetal_heart_NbHH19W *Homo sapiens* cDNA clone IMAGE:364905 3-, mRNA Sequence, [Aug. 13, 1996] (online); [retrieved on Sep. 10, 2014]; GenBank Accession No. AA024504; <URL:http://www.ncbinlm.nih.gov/nucest/AA024504> (2 pages).
1M0356A24F Mouse 10kb Plasmid UUGC1M Library Mus Musculus Genomic Clone UUGC1M0356A24 F, Genomic Survey Sequence, [Oct. 5, 2000] (online); [retrieved on Sep. 10, 2014]; GenBank Accession No. AZ511352; <URL:http//www.ncbi.nlm.nih.gov/nucgss/az511352> (2 pages).
zt65b07.r1 Soares_testis_NHT *Homo sapiens* cDNA Clone IMAGE:727189 5-Similar to Contains Alu Repetitive Element; Contains Element LTR3 Repetitive Element; mRNA Sequence, [May 16, 1997] (online); [retrieved on Sep. 10, 2014]; GenBank Accession No. AA293828; <URL: http://www.ncbi.nlm.nih.gov/nucest/AA293828> (2 pages).
Macaca Mulatta Isolate rq2277-15q15.2 MLV-Derived Vector Proviral Integration Site, [Mar. 2, 2005] (online); [retrieved on Sep. 10, 2014]; GenBank Accession No. AY733983; <URL: http://www.ncbi.nlm.nih.gov/nuccore/AY733983> (1 page).
*Oryza sativa* Subsp. *Indica* Microsatellite Marker RM288, Sequence Tagged Site, [Aug. 13, 2001] (online); [retrieved on Sep. 10, 2014]; GenBank Accession No. AF344114; <URL: http://www.ncbi.nlm.nih.gov/nuccore/AF344114> (1 page).
Huang et al., "Enrichment of Microsatellite DNAs Using Triplex Affinity Capture in Chamaecyparis Obtusa," J. Jpn. For. Soc. 2005, vol. 87, No. 2, pp. 153-156.
Danio Rerio Genomic Clone DKEY-23O6, Genomic Survey Sequence, [Nov. 25, 2002] (online); [retrieved on Sep. 10, 2014]; GenBank Accession No. AL979061; <URL: http://www.ncbi.nlm.nih.gov/nucgss/AL979061> (1 page).
67ETGS_T3_002_G03_15JAN2004_019 Germinating Seed Library 67ETGS Brassica Napus cDNA 5-, mRNA Sequence, [Jun. 30, 2007] (online); retrieved on Sep. 10, 2014]; GenBank Accession No. EE439266; <URL: http//www.ncbi.nlm.nih.gov//nucest/EE439266> (1 page).
Gallus gallus DNA, Microsatellite Locus GUC0010, [Aug. 21, 2008] (online); retrieved on Sep. 10, 2014]; GenBank Accession No. AB063270; <URL: http//www.ncbi.nlm.nih.gov/nuccore/AB063270> (1 page).

(Continued)

*Primary Examiner* — Tracy Vivlemore
(74) *Attorney, Agent, or Firm* — Wilmer Cutler Pickering Hale and Dorr LLP

(57) ABSTRACT

The present invention provides a novel nucleic acid molecule that can be used for detection of peanuts. The peanut-binding nucleic acid molecule of the present invention is characterized in that it binds to a peanut allergen with a dissociation constant of 10 nM or less, and preferably contains a polynucleotide consisting of any of base sequences of SEQ ID NOs: 1 to 15, for example. It is also preferable that, for example, the peanut-binding nucleic acid molecule of the present invention binds with significant specificity to the peanut allergen rather than to a soybean protein.

10 Claims, 16 Drawing Sheets

(56) References Cited

OTHER PUBLICATIONS

1M0080H01F Mouse 10kb Plasmid UUGC1M Library Mus Musculus Genomic Clone UUGC1M0080H01 F, Genomic Survey Sequence, [Sep. 29, 2000] (online); retrieved on [Sep. 10, 2014]; GenBank Accession No. AZ345505; <URL: http://www.ncbi.nlm.nih.gov/nucgss/AZ345505> (2 pages).
Tran et al., "Selection of Aptamers Against Ara h 1 Protein for FO-SPR Biosensing of Peanut Allergens in Food Matrices," Biosensors and Bioelectronics, 2013, vol. 43, pp. 245-251.
Pérez-Ruiz et al., "Probing the Force-Induced Dissociation of Aptamer-Protein Complexes," Analytical Chemistry, 2014, vol. 86, pp. 3084-3091.
Japanese Office Action issued by the Japan Patent Office in the Japanese Application No. 2015-551399 dated Feb. 16, 2017 (17 pages).
Yotsuhashi, K., et al., "Research on peanut proteins (second report): dissociation of conarachin to subunits," Journal of the Japanese Society of Food Science and Technology, vol. 20, No. 7, pp. 327-330 (1973).
Extended European Search Report issued by the European Patent Office for European Application No. 14867903.8 dated Jul. 4, 2017 (9 pages).
Gupta, S., et al., "Sequence-based novel genomic microsatellite markers for robust genotyping purposes in foxtail millet," Plant Cell Reports, vol. 31, No. 2, pp. 323-337 (Oct. 13, 2011).
Lakshmipriya, T., et al., "Generation of Anti-Influenza Aptamers Using the Systematic Evolution of Ligands by Exponential Enrichment for Sensing Applicaitons," Langmuir, vol. 29, No. 48, pp. 15107-15115 (Dec. 3, 2013).
Vieira, E. S. N., et al., "Development of microsatellite markers for identifying Brazilian Coffea arabica varieties," Genetics and Molecular Biology, vol. 33, No. 3, pp. 507-514 (Jan. 2010).
Zhao, X.-Q., et al., "Single-Molecule Force Spectroscopic Studies on Intra- and Intermolecular Interactions of G-Quadruplex Aptamer with Target Shp2 Protein," Journal of Physical Chemistry Part B: Condensed Matter, Materials, Surfaces, Interfaces & Biophysical, vol. 116, No. 37, pp. 11397-11404 (Sep. 20, 2012).

* cited by examiner

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: aptamer

<400> SEQUENCE: 1
cccgcctgta ttcctgtcc                                                19

<210> SEQ ID NO 2
<211> LENGTH: 31
<212> TYPE: DNA
<213> ORGANISM: Artificial Sequence
<220> FEATURE:
<223> OTHER INFORMATION: aptamer

<400> SEQUENCE: 2
gaatccgcgg ggtagcggtg gcgagcgatt c                                  31

<210> SEQ ID NO 3
<211> LENGTH: 32
<212> TYPE: DNA
<213> ORGANISM: Artificial Sequence
<220> FEATURE:
<223> OTHER INFORMATION: aptamer

<400> SEQUENCE: 3
gttcgtggtg tgttgtgtgt gattccaggg ac                                 32

<210> SEQ ID NO 4
<211> LENGTH: 24
<212> TYPE: DNA
<213> ORGANISM: Artificial Sequence
<220> FEATURE:
<223> OTHER INFORMATION: aptamer

<400> SEQUENCE: 4
gttttctagg ccaatctgat caac                                          24

<210> SEQ ID NO 5
<211> LENGTH: 20
<212> TYPE: DNA
<213> ORGANISM: Artificial Sequence
<220> FEATURE:
<223> OTHER INFORMATION: aptamer

<400> SEQUENCE: 5
tttttttttt tttttttttt                                               20

<210> SEQ ID NO 6
<211> LENGTH: 25
<212> TYPE: DNA
<213> ORGANISM: Artificial Sequence
```

```
<220> FEATURE:
<223> OTHER INFORMATION: aptamer

<400> SEQUENCE: 6
ctctctctct ctccctctct ctctc                                          25

<210> SEQ ID NO 7
<211> LENGTH: 74
<212> TYPE: DNA
<213> ORGANISM: Artificial Sequence
<220> FEATURE:
<223> OTHER INFORMATION: aptamer

<400> SEQUENCE: 7
ggattccgtg ccgtgctaaa ggcctccccg tttataggca ggtatccggc agactactgg    60
gcttgcgaca aatg                                                      74

<210> SEQ ID NO 8
<211> LENGTH: 26
<212> TYPE: DNA
<213> ORGANISM: Artificial Sequence
<220> FEATURE:
<223> OTHER INFORMATION: aptamer

<400> SEQUENCE: 8
tctctacccc ccaccgccca cgactc                                         26

<210> SEQ ID NO 9
<211> LENGTH: 25
<212> TYPE: DNA
<213> ORGANISM: Artificial Sequence
<220> FEATURE:
<223> OTHER INFORMATION: aptamer

<400> SEQUENCE: 9
ctctctctcc ccccccccct ctctc                                          25

<210> SEQ ID NO 10
<211> LENGTH: 25
<212> TYPE: DNA
<213> ORGANISM: Artificial Sequence
<220> FEATURE:
<223> OTHER INFORMATION: aptamer

<400> SEQUENCE: 10
ctctctctct cccccctct ctctc                                           25

<210> SEQ ID NO 11
<211> LENGTH: 25
<212> TYPE: DNA
<213> ORGANISM: Artificial Sequence
<220> FEATURE:
<223> OTHER INFORMATION: aptamer

<400> SEQUENCE: 11
ctctctctct ctctctctct ctctc                                          25

<210> SEQ ID NO 12
<211> LENGTH: 26
<212> TYPE: DNA
<213> ORGANISM: Artificial Sequence
<220> FEATURE:
<223> OTHER INFORMATION: aptamer

<400> SEQUENCE: 12
```

-continued

```
cacacacacc cccccccca cacaca                                      26

<210> SEQ ID NO 13
<211> LENGTH: 26
<212> TYPE: DNA
<213> ORGANISM: Artificial Sequence
<220> FEATURE:
<223> OTHER INFORMATION: aptamer

<400> SEQUENCE: 13
cacacacaca cccccccaca cacaca                                     26

<210> SEQ ID NO 14
<211> LENGTH: 26
<212> TYPE: DNA
<213> ORGANISM: Artificial Sequence
<220> FEATURE:
<223> OTHER INFORMATION: aptamer

<400> SEQUENCE: 14
cacacacaca cacccacaca cacaca                                     26

<210> SEQ ID NO 15
<211> LENGTH: 26
<212> TYPE: DNA
<213> ORGANISM: Artificial Sequence
<220> FEATURE:
<223> OTHER INFORMATION: aptamer

<400> SEQUENCE: 15
cacacacaca cacacacaca cacaca                                     26

<210> SEQ ID NO 16
<211> LENGTH: 26
<212> TYPE: DNA
<213> ORGANISM: Artificial Sequence
<220> FEATURE:
<223> OTHER INFORMATION: aptamer

<400> SEQUENCE: 16
tctctacccc ccaccgccca cgactc                                     26
```

PEANUT-BINDING NUCLEIC ACID MOLECULE AND USE THEREOF

CROSS-REFERENCE TO RELATED APPLICATIONS

This application is a national stage application of International Application No. PCT/JP2014/067022 entitled "Peanut-Binding Nucleic Acid Molecule and Use Thereof," filed on Jun. 26, 2014, which claims priority to Japanese Patent Application No. 2013-251477, filed on Dec. 4, 2013. The disclosures of each which are hereby incorporated by reference in their entirety.

TECHNICAL FIELD

The present invention relates to a nucleic acid molecule that binds to peanuts and use thereof.

BACKGROUND ART

Peanuts (*Arachis hypogaea*), hens' eggs, and milk are well-known three common allergens in the United States. Among them, peanuts (especially their seeds) cause serious allergy symptoms including anaphylactic shock, which may be fatal. Besides, peanuts have other problems in that they can induce allergic responses even when they are present in a small amount, and that heat-treated peanuts exhibit enhanced allergenicity. On this account, it is very important to check the presence of peanuts as a raw material in processed foods, manufacturing lines thereof, etc.

Allergens, which are substances causing allergies, generally are proteins and degradation products thereof (peptides), and the mainstream approach for analyzing the allergens is to use antibodies against the allergens as antigens. As for peanuts, there has been reported a method for detecting peanut allergens using an antibody against an Ara h1 protein, which is a major allergen in peanut seeds, for example (Patent Document 1).

However, it is difficult to provide a simple and low-cost test method using an antibody because the antibody, which is a protein, has a problem in stability. On this account, in recent years, a nucleic acid molecule that specifically binds to an antigen is attracting attention as a substitute for an antibody. However, no nucleic acid molecule that binds to peanut allergens has been reported heretofore. Furthermore, even a small amount of peanuts can be harmful as described above. Thus, there is a demand for improvement in specificity and accuracy of analysis.

CITATION LIST

Patent Document(s)

[Patent Document 1] JP 2009-271091 A

SUMMARY OF THE INVENTION

Problems to be Solved by the Invention

With the foregoing in mind, it is an object of the present invention is to provide a novel nucleic acid molecule that can be used for detection of peanuts.

Means for Solving Problem

The present invention provides a peanut-binding nucleic acid molecule that binds to a peanut allergen with a dissociation constant of 10 nM or less.

The present invention also provides a peanut detection sensor including: the peanut-binding nucleic acid molecule according to the present invention.

The present invention also provides a method for detecting a peanut, including the step of: detecting a peanut allergen in a sample by causing the sample and the peanut-binding nucleic acid molecule according to the present invention to come into contact with each other to bind the peanut allergen in the sample and the nucleic acid molecule.

Effects of the Invention

The peanut-binding nucleic acid molecule of the present invention can bind to a peanut allergen with the above-described dissociation constant. Thus, according to the peanut-binding nucleic acid molecule of the present invention, a peanut allergen in a sample can be detected with high accuracy on the basis of the presence or absence of the binding with the peanut allergen, for example. Therefore, it can be said that the peanut-binding nucleic acid molecule of the present invention is a very useful tool for the detection of peanut allergens in the fields of food manufacturing, food management, food distribution, and the like, for example.

DESCRIPTION OF EXEMPLARY EMBODIMENTS

Figure 1:
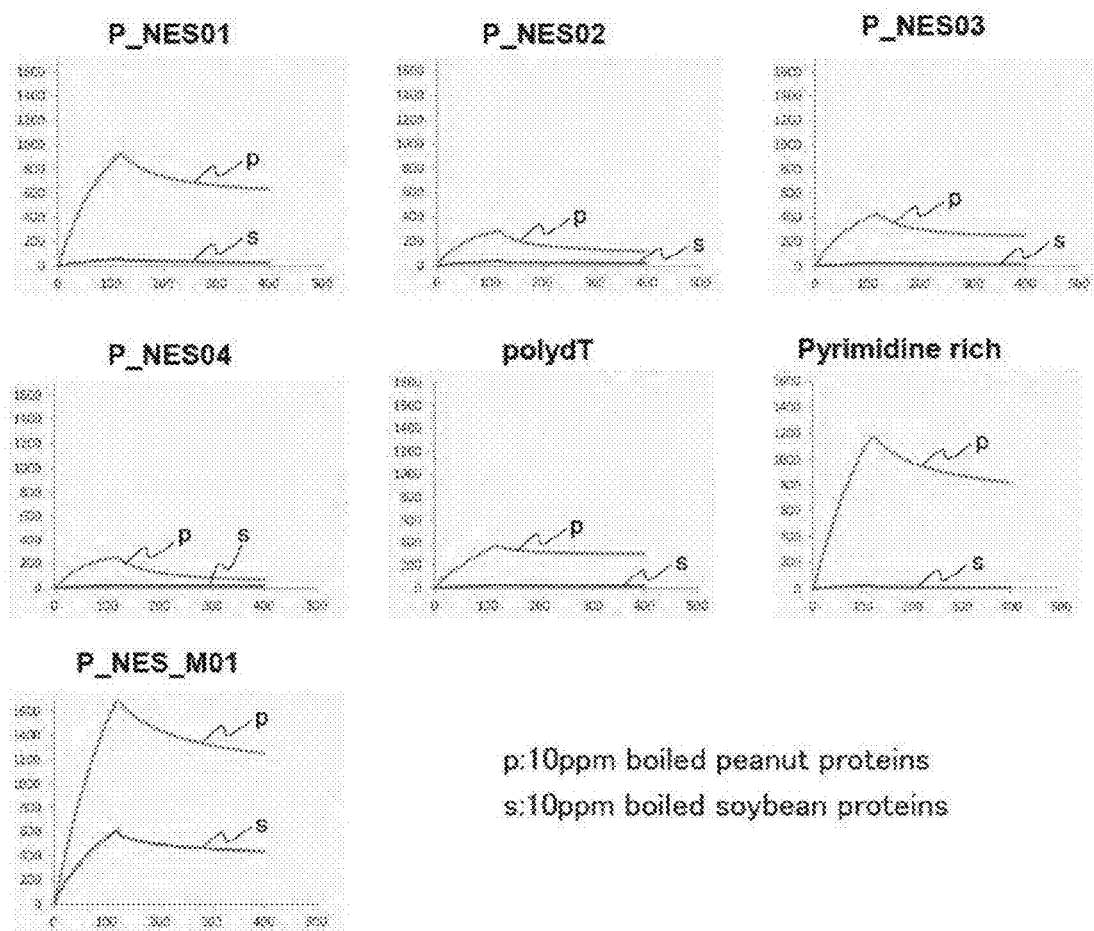
FIG. 1 shows graphs showing the binding ability of aptamers to peanut proteins in Example 1 of the present invention.

In the nucleic acid molecule of the present invention, the peanut allergen is conarachin or a subunit thereof, for example.

In the nucleic acid molecule of the present invention, the subunit is Ara h1, for example.

In the nucleic acid molecule of the present invention, the peanut allergen is an undenatured allergen or a heat-denatured allergen, for example.

The nucleic acid molecule of the present invention binds with significant specificity to the peanut allergen rather than a soybean protein, for example.

The nucleic acid molecule of the present invention binds to a soybean protein with a dissociation constant of more than 10 nM, for example.

In the nucleic acid molecule of the present invention, the soybean protein is β-conglycinin, for example.

In the nucleic acid molecule of the present invention, a detectable concentration for the peanut allergen is 10 ppm or more, for example.

The nucleic acid molecule of the present invention includes, for example, at least one polynucleotide selected from the group consisting of the following polynucleotides (a) to (d):
(a) a polynucleotide consisting of any of base sequences of SEQ ID NOs: 1 to 15;
(b) a polynucleotide that consists of a base sequence obtained by deletion, substitution, insertion, and/or addition of one or more bases in any of the base sequences of the polynucleotide (a) and binds to the peanut allergen;
(c) a polynucleotide that consists of a base sequence with an identity of at least 80% to any of the base sequences of the polynucleotide (a) and binds to the peanut allergen; and
(d) a polynucleotide that consists of a base sequence complementary to a polynucleotide hybridizing to any of the base sequences of the polynucleotide (a) under stringent conditions and binds to the peanut allergen.

The nucleic acid molecule of the present invention includes, for example, the following polynucleotide (e):
(e) a polynucleotide consisting of a pyrimidine-rich base sequence.

In the nucleic acid molecule of the present invention, the polynucleotide is a DNA, for example.

In the nucleic acid molecule of the present invention, the polynucleotide includes a modified base, for example.

The detection sensor of the present invention further includes a nucleic acid molecule that forms a G-quartet structure, for example.

In the detection sensor of the present invention, the nucleic acid molecule that forms a G-quartet structure is a DNAzyme or an RNAzyme, for example.

The detection sensor of the present invention further includes a porphyrin, for example.

In the detection method of the present invention, the sample is at least one selected from the group consisting of foods, food ingredients, and food additives, for example.

(1) Peanut-Binding Nucleic Acid Molecule

As described above, the peanut-binding nucleic acid molecule of the present invention is characterized in that it binds to a peanut allergen with a dissociation constant of 10 nM or less.

Peanuts are plants belonging to the genus *Arachis* of the family Fabaceae, and their scientific name is *Arachis hypogaea*. In the present invention, peanut allergens are contained in the whole or a part of the individual peanut plant, for example. The part of the individual peanut plant may be an organ, a tissue, or a cell, for example. The organ may be, for example, a seed, fruit, petal, corolla, flower, leaf, stem (underground stem), root, or bulbil. In the present invention, it is preferable that the peanut allergen is the one contained particularly in the seed of the peanut.

The nucleic acid molecule of the present invention binds to conarachin, which is a major peanut allergen, or a subunit thereof, for example. Examples of the conarachin include conarachin I and conarachin II (α-conarachin). Examples of the subunit of the conarachin include Ara h1. It is said that conarachin accounts for about 17% of the total amount of peanut proteins in a peanut seed with its skin being removed. Ara h1 is the β subunit of the conarachin, and is a glycopeptide with a trimmer structure.

The peanut allergen may be an undenatured allergen without denaturation by heating or a denatured allergen with denaturation by heating, for example. The nucleic acid molecule of the present invention can bind to both undenatured and denatured allergens, for example. As described above, the allergenicity of peanuts is enhanced by heating. Food manufacturing and the like often involve heat treatments. Thus, the nucleic acid molecule of the present invention that binds to denatured allergens is particularly preferable.

The nucleic acid molecule of the present invention binds to the peanut allergen with a dissociation constant of 10 nM or less, preferably 1 nM or less, and more preferably 0.1 nM or less. The minimum detectable concentration of the peanut allergen by the nucleic acid molecule of the present invention is, for example, 5 nM, 10 nM, 100 nM, or 1000 nM.

The binding between the nucleic acid molecule of the present invention and the peanut allergen can be determined by, for example, surface plasmon resonance molecular interaction (SPR; Surface Plasmon Resonance) analysis or the like. The analysis can be performed using ProteON (trade name, BioRad), for example.

The nucleic acid molecule of the present invention binds with significant specificity to the peanut allergen rather than soybean proteins, for example. That is, it can be said that the binding properties of the nucleic acid molecule of the present invention to the peanut allergen are more significant than the binding properties to soybean proteins. A major peanut allergen (e.g., conarachin) is similar to a soybean protein (e.g., β-conglycinin, in particular) with the gene sequence homology between them being about 45%. Thus, in detection of a peanut allergen using a substance that binds to the peanut allergen, the substance may bind to a soybean protein, resulting in a false positive test result. However, the nucleic acid molecule of the present invention binds with significant specificity to the peanut allergen rather than soybean proteins and thus can reduce the influence of false positive.

The nucleic acid molecule of the present invention binds to Ara h1 with a dissociation constant of 10 nM or less, 1 nM or less, 0.2 nM or less, 0.15 nM or less, or 0.1 nM or less, for example, and the range of the dissociation constant may be, for example, from 0.2 to 0.15 nM. The minimum detectable concentration of Ara h1 by the nucleic acid molecule of the present invention is, for example, 5 nM, 6 nM, 10 nM, 12.5 nM, 25 nM, or 50 nM.

The minimum detectable concentration of conarachin by the nucleic acid molecule of the present invention is, for example, 5 nM, 6 nM, 10 nM, 25 nM, 50 nM, 100 nM, or 1000 nM. As a specific example, the minimum detectable concentration of heat-denatured conarachin is, for example, 5 nM, 6 nM, 10 nM, 25 nM, or 50 nM.

The minimum detectable concentration of peanut proteins by the nucleic acid molecule of the present invention is, for example, 3 ppm, 5 ppm, 10 ppm, 30 ppm, or 50 ppm. As a specific example, the minimum detectable concentration of heat-denatured peanut proteins is, for example, 3 ppm or 10 ppm.

The minimum detectable concentration of soybean proteins by the nucleic acid molecule of the present invention is, for example, more than 10 nM, or alternatively, 100 nM, 1000 nM, or undetectable (no binding with the soybean proteins). As a specific example, the minimum detectable concentration of β-conglycinin is, for example, more than 100 nM, or alternatively, 300 nM, 1000 nM, or undetectable (no binding with β-conglycinin).

The nucleic acid molecule of the present invention can detect the peanut allergen in a sample in which the content of the peanut allergen (the amount of the protein) in the total amount of proteins is, for example, 10 ppm or more, preferably 3 ppm or more, or more preferably 1 ppm or more. As a specific example, the nucleic acid molecule of the present invention can detect conarachin in a sample in which the content of the conarachin in the total amount of proteins is 10 ppm or more, 3 ppm or more, or 1 ppm or more, for example.

Specific examples of the peanut-binding nucleic acid molecule of the present invention are shown below. The nucleic acid molecule of the present invention is, for example, a nucleic acid molecule containing at least one polynucleotide selected from the group consisting of the following polynucleotides (a) to (d):
(a) a polynucleotide consisting of any of base sequences of SEQ ID NOs: 1 to 15;
(b) a polynucleotide that consists of a base sequence obtained by deletion, substitution, insertion, and/or addition of one or more bases in any of the base sequences of the polynucleotide (a) and binds to the peanut allergen;
(c) a polynucleotide that consists of a base sequence with an identity of at least 80% to any of the base sequences of the polynucleotide (a) and binds to the peanut allergen; and
(d) a polynucleotide that consists of a base sequence complementary to a polynucleotide hybridizing to any of the base sequences of the polynucleotide (a) under stringent conditions and binds to the peanut allergen.

In the nucleic acid molecule of the present invention, the building blocks of the polynucleotides (a) to (d) are, for example, nucleotide residues, examples of which include deoxyribonucleotide residues and ribonucleotide residues. The polynucleotide is, for example, DNA consisting of deoxyribonucleotide residues or DNA including a deoxyribonucleotide residue(s) and a ribonucleotide residue(s), and the polynucleotide may further include a non-nucleotide residue(s), as described below. The peanut-binding nucleic acid molecule of the present invention also is referred to as "DNA aptamer" hereinafter, for example.

The nucleic acid molecule according to the present invention may consist of any of the polynucleotides (a) to (d) or may include any of the polynucleotides (a) to (d), for example. In the latter case, the nucleic acid molecule of the present invention may include, for example, two or more polynucleotides selected from the polynucleotides (a) to (d), as described below. The two or more polynucleotides may be the polynucleotides with the same sequence or different sequences. Also, in the latter case, the nucleic acid molecule of the present invention further may include a linker(s) and/or an additional sequence(s), for example.

The polynucleotide (a) consists of any of the base sequences of SEQ ID NOs: 1 to 15.

P_NES01 (NAH1128R7Am2s19G)
SEQ ID NO: 1
CCCGCCTGTATTCCTGTCC

P_NES02 (CONA161R8m1s31)
SEQ ID NO: 2
GAATCCGCGGGGTAGCGGTGGCGAGCGATTC

P_NES03 (CONA161R2R8m1s32)
SEQ ID NO: 3
GTTCGTGGTGTGTTGTGTGTGATTCCAGGGAC

P_NES04 (CONA171NNHR2R8m2s24)
SEQ ID NO: 4
GTTTTCTAGGCCAATCTGATCAAC

PolydT20
SEQ ID NO: 5
TTTTTTTTTTTTTTTTTTTT

CT25_C3 (Pyrimidine rich)
SEQ ID NO: 6
CTCTCTCTCTCTCCCTCTCTCTCTC

P_NES_M01 (CONA170TEDAR2R8m1)
SEQ ID NO: 7
GGATTCCGTGCCGTGCTAAAGGCCTCCCC

GTTTATAGGCAGGTATCC

GGCAGACTACTGGGCTTGCGACAAATG

NAH1121NNH200R7m1s26
SEQ ID NO: 8
TCTCTACCCCCACCGCCCACGACTC

CT25_C11
SEQ ID NO: 9
CTCTCTCTCCCCCCCCCCCTCTCTC

CT25_C7
SEQ ID NO: 10
CTCTCTCTCTCCCCCCCTCTCTCTC

CT25_C0
SEQ ID NO: 11
CTCTCTCTCTCTCTCTCTCTCTCTC

CA25_C11
SEQ ID NO: 12
CACACACACCCCCCCCCCACACACA

CA25_C7
SEQ ID NO: 13
CACACACACACCCCCCCACACACACA

CA25_C3
SEQ ID NO: 14
CACACACACACACCCACACACACACA

CA25_C0
SEQ ID NO: 15
CACACACACACACACACACACACACA

Regarding the polynucleotide (b), the term "one or more" is not limited as long as, for example, it is in the range where the polynucleotide (b) binds to the peanut allergen. The "one or more" bases in any of the base sequences of the polynucleotide (a) are, for example, 1 to 10, 1 to 7, 1 to 5, 1 to 3, or 1 or 2 bases. In the present invention, the numerical range regarding the number of bases, sequences, or the like discloses, for example, all the positive integers falling within that range. That is, for example, the description "one to five bases" discloses all of "one, two, three, four, and five bases" (the same applies hereinafter).

Regarding the polynucleotide (c), the "identity" is not limited as long as, for example, it is in the range where the polynucleotide (c) binds to the peanut allergen. The identity is, for example, at least 80%, at least 85%, at least 90%, at least 95%, at least 96%, at least 97%, at least 98%, or at least 99%. The identity can be calculated with analysis software such as BLAST or FASTA using default parameters, for example (the same applies hereinafter).

Regarding the polynucleotide (d), the "polynucleotide hybridizing to" is, for example, a polynucleotide perfectly or partially complementary to the polynucleotide (a). The hybridization can be detected by various types of hybridization assay, for example. The hybridization assay is not particularly limited, and for example, a method described in "Molecular Cloning: A Laboratory Manual $2^{nd}$ Ed." edited by Sambrook et al. (Cold Spring Harbor Laboratory Press [1989]) or the like can be employed.

Regarding the polynucleotide (d), the "stringent conditions" may be any of low stringency conditions, medium stringency conditions, and high stringency conditions, for example. The "low stringency conditions" are, for example, conditions where 5×SSC, 5×Denhardt's solution, 0.5% SDS, and 50% formamide are used at 32° C. The "medium stringency conditions" are, for example, conditions where 5×SSC, 5×Denhardt's solution, 0.5% SDS, and 50% formamide are used at 42° C. The "high stringency conditions" are, for example, conditions where 5×SSC, 5×Denhardt's solution, 0.5% SDS, and 50% formamide, are used at 50° C. Those skilled in the art can set the degree of stringency by, for example, setting the conditions such as the temperature, the salt concentration, the concentration and length of a probe, the ionic strength, the time, etc. as appropriate. As the "stringent conditions", it is also possible to employ conditions described in the above-described "Molecular Cloning: A Laboratory Manual $2^{nd}$ Ed." edited by Sambrook et al. (Cold Spring Harbor Laboratory Press [1989]) or the like, for example.

The nucleic acid molecule of the present invention may contain the following polynucleotide (e), for example.

(e) a polynucleotide consisting of a pyrimidine-rich base sequence

The polynucleotide (e) contains nucleotides with pyrimidine bases abundantly, and the proportion of pyrimidine bases in all the bases in the polynucleotide is, for example, 50% or more, 60% or more, 80% or more, or 100%. The length of the polynucleotide (e) is, for example, 19- to 74-mer, 19- to 50-mer, or 19- to 40-mer. In the polynucleotide (e), the type of the pyrimidine base is not particularly limited, and examples thereof include cytosine, thymine, and uracil. Among them, cytosine and thymine are preferable. The polynucleotide (e) may contain only one type, two types, or three types of pyrimidine bases, for example. Specific examples of the polynucleotide (e) include a polynucleotide having only thymine as the bases and a polynucleotide having only cytosine as the bases. The former polynucleotide is, for example, the above-described polynucleotide of SEQ ID NO: 5 or a polynucleotide of SEQ ID NO: 6 in which all the cytosine bases are substituted with thymine bases. The latter polynucleotide is, for example, a polynucleotide consisting of a base sequence of SEQ ID NO: 5 or SEQ ID NO: 6 in which all the thymine bases are substituted with cytosine bases. The polynucleotide (e) may be a polynucleotide having thymine and cytosine as the bases, for example, and specific examples thereof include the polynucleotide consisting of the base sequence of SEQ ID NO: 6.

Examples of the polynucleotide (e) include the above-described polynucleotides consisting of the base sequences of SEQ ID NOs: 9 to 15.

The nucleic acid molecule according to the present invention may include, for example, any one sequence selected from the polynucleotides (a) to (e), or a plurality of sequences selected from the polynucleotides (a) to (e). In the latter case, it is preferable that the plurality of polynucleotide sequences are linked to each other to form a single-stranded polynucleotide. The plurality of polynucleotide sequences may be linked to each other directly, or may be linked to each other indirectly with a linker, for example. It is preferable that the polynucleotide sequences are linked to each other directly or indirectly at their ends. The plurality of polynucleotide sequences may be the same or different from each other, for example. Preferably, the plurality of polynucleotide sequences are the same, for example. When the nucleic acid molecule of the present invention includes the plurality of polynucleotide sequences, the number of the sequences is not particularly limited. The number of the sequences is 2 or more, for example, and specifically is 2 to 20, 2 to 10, or 2 or 3.

The linker is not particularly limited. The length of the linker is not particularly limited, and is, for example, 1- to 200-mer, 1- to 20-mer, 3- to 12-mer, or 5- to 9-mer. The building blocks of the linker are, for example, nucleotide residues, examples of which include deoxyribonucleotide residues and ribonucleotide residues. The linker is not particularly limited, and examples thereof include polynucleotides such as DNA consisting of deoxyribonucleotide residues and DNA including a ribonucleotide residue(s). Specific examples of the linker include polydeoxythymine (poly(dT)), polydeoxyadenine (poly(dA)), and poly(dA-dT) having a repetitive sequence composed of A and T. Preferably, the linker is poly(dT) or poly(dA-dT).

In the nucleic acid molecule of the present invention, the polynucleotide preferably is a single-stranded polynucleotide. It is preferable that the single-stranded polynucleotide can form a stem structure and a loop structure by self-annealing, for example. It is preferable that the polynucleotide can form a stem-loop structure, an internal loop structure, and/or a bulge structure, for example.

The nucleic acid molecule of the present invention may be a double strand, for example. When the nucleic acid molecule is a double strand, for example, one of single-stranded polynucleotides includes any of the polynucleotides (a) to (e), and the other single-stranded polynucleotide is not limited. The other single-stranded polynucleotide may be, for example, a polynucleotide including a base sequence complementary to any of the polynucleotides (a) to (e). When the nucleic acid molecule of the present invention is a double strand, it is preferable to dissociate the double strand to single-stranded polynucleotides by denaturation or the like before use, for example. Also, it is preferable that the dissociated single-stranded polynucleotide including any of the polynucleotides (a) to (e) is forming a stem structure and a loop structure as described above, for example.

In the present invention, the expression "can form a stem structure and a loop structure" encompasses that, for example, a stem structure and a loop structure are formed actually, and also, even if a stem structure and a loop structure are not formed, they can be formed depending on conditions. The expression "can form a stem structure and a loop structure (and grammatical variations thereof)" encompasses, for example, both the cases where the formation thereof has been confirmed through an experiment and where the formation thereof is predicted through simulation using a computer or the like.

The building blocks of the nucleic acid molecule of the present invention are, for example, nucleotide residues.

Examples of the nucleotide residues include deoxyribonucleotide residues and ribonucleotide residues. Examples of the nucleic acid molecule of the present invention include DNA consisting of deoxyribonucleotide residues only and DNA including one or more ribonucleotide residues. In the latter case, "one or more" is not particularly limited. For example, the number of the ribonucleotide residues in the polynucleotide is, for example, 1 to 91, 1 to 30, 1 to 15, 1 to 7, 1 to 3, or 1 or 2.

The polynucleotide may contain a modified base(s). The modified base is not particularly limited, and may be, for example, a modified natural base (non-artificial base), which preferably has a similar function to the natural base. The natural base is not particularly limited, and may be, for example, a purine base with a purine skeleton, a pyrimidine base with a pyrimidine skeleton, or the like. The purine base is not particularly limited, and examples thereof include adenine (a) and guanine (g). The pyrimidine base is not particularly limited, and examples thereof include cytosine (c), thymine (t), and uracil (u). The modified site in the base is not particularly limited. When the base is a purine base, the modified site in the purine base may be, for example, the 7-position or the 8-position in the purine skeleton. When the base is a pyrimidine base, the modified site in the pyrimidine base may be, for example, the 5-position or the 6-position in the pyrimidine skeleton. When the pyrimidine skeleton has "=O" bound to the carbon at the 4-position and a group that is not "—CH$_3$" or "—H" bound to the carbon at the 5-position, the modified base can be referred to as modified uracil or modified thymine.

The modified group in the modified base is not particularly limited, and may be, for example, a methyl group, a fluoro group, an amino group, a thio group, a benzylaminocarbonyl group represented by the following formula (1), a tryptaminocarbonyl group represented by the following formula (2), or an isobutylaminocarbonyl group.

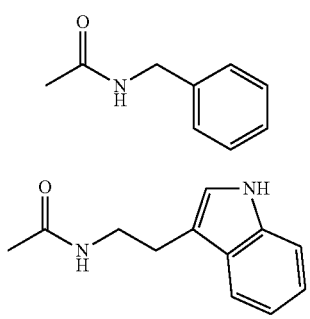

The modified base is not particularly limited, and examples thereof include: modified adenine, which is adenine with modification; modified thymine, which is thymine with modification; modified guanine, which is guanine with modification; modified cytosine, which is cytosine with modification; and modified uracil, which is uracil with modification. Among them, the modified thymine, the modified uracil, and the modified cytosine are preferable.

Specific examples of the modified adenine include 7'-deazaadenine.

Specific examples of the modified guanine include 7'-deazaguanine.

Specific examples of the modified thymine include 5'-benzylaminocarbonyl thymine, 5'-tryptaminocarbonyl thymine, and 5'-isobutylaminocarbonyl thymine.

Specific examples of the modified uracil include 5'-benzylaminocarbonyl uracil (BndU), 5'-tryptaminocarbonyl uracil (TrpdU), and 5'-isobutylaminocarbonyl uracil.

The polynucleotide may contain, for example, only one type or two or more types of the modified bases.

The number of the modified bases is not particularly limited. In the polynucleotide, the number of the modified bases is not particularly limited. The number of the modified base in the polynucleotide may be, for example, 1 to 100, preferably 1 to 90, more preferably 1 to 80, still more preferably 1 to 70, and particularly preferably 1 to 60, 40, or 27. Alternatively, all the bases may be the modified bases. The number of the modified bases may be, for example, the number of the modified bases of any one type, or may be the total number of the modified bases of two or more types.

When the polynucleotide contains the modified base(s), the proportion of the modified base(s) is not particularly limited. The proportion of the modified base(s) in the total number of the bases in the polynucleotide is, for example, 1/100 or more, 1/40 or more, 1/20 or more, 1/10 or more, 1/4 or more, or 1/3 or more. The proportion of the modified base(s) is represented by a fraction, with the total number of the bases and the number of the modified bases satisfying the fraction both being positive integers.

The above-described polynucleotide consisting of the base sequence of SEQ ID NO: 7 preferably contains the modified base(s), and in particular, it is preferable that at least one thymine base is the modified thymine. In the above-described polynucleotide of SEQ ID NO: 7, the number of the modified thymine bases is not particularly limited, and the lower limit thereof is, for example, 1, 3, or 5, and the upper limit thereof is, for example, 17, 15, or 13. Alternatively, all the thymine bases may be the modified thymine bases.

In the polynucleotide of SEQ ID NO: 7, the proportion of the modified thymine base(s) is not particularly limited. The proportion of the modified thymine base(s) in the total number of the natural thymine bases and the modified thymine base(s) is, for example, 1/100 or more, 1/40 or more, 1/20 or more, 1/10 or more, 1/4 or more, or 1/3 or more.

The nucleic acid molecule of the present invention may include a modified nucleotide(s), for example. The modified nucleotide may be a nucleotide having the above-described modified base, a nucleotide having a modified sugar obtained through modification of a sugar residue, or a nucleotide having the modified base and the modified sugar.

The sugar residue is not particularly limited, and may be a ribose residue or a deoxyribose residue, for example. The modified site in the sugar residue is not particularly limited, and may be, for example, the 2'-position or the 4'-position in the sugar residue. Either one or both of the 2'-position and the 4'-position may be modified. Examples of a modifying group in the modified sugar include methyl groups, fluoro groups, amino groups, and thio groups.

In the case where the base in the modified nucleotide residue is a pyrimidine base, it is preferable that the 2'-position and/or the 4'-position in the sugar residue is modified, for example. Specific examples of the modified nucleotide residue include modified nucleotide residues with the 2'-position in the deoxyribose residue or ribose residue being modified, such as a 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil nucleotide residue, 2'-aminated-cytosine nucleotide residue, 2'-thiated-uracil nucleotide residue, and 2'-thiated-cytosine nucleotide residue.

The number of the modified nucleotides is not particularly limited. For example, the number of the modified nucleotides in the polynucleotide is, for example, 1 to 100, 1 to 90, 1 to 80, or 1 to 70. Also, the number of the modified nucleotides in the full-length nucleic acid molecule containing the polynucleotide is not particularly limited. The number of the modified nucleotides is, for example, 1 to 91 or 1 to 78, and specifically, the range thereof is the same as the above-described range, for example.

The nucleic acid molecule of the present invention may contain, for example, one or more artificial nucleic acid monomer residues. The term "one or more" is not particularly limited, and may be, for example, 1 to 100, 1 to 50, 1 to 30, or 1 to 10 in the polynucleotide, for example. Examples of the artificial nucleic acid monomer residue include PNAs (Peptide Nucleic Acids), LNAs (Locked Nucleic Acids), and ENAs (2'-O,4'-C-Ethylenebridged Nucleic Acids). The nucleic acid in the monomer residue is the same as described above, for example.

It is preferable that the nucleic acid molecule of the present invention is resistant to nuclease, for example. In order to allow the nucleic acid molecule to have nuclease resistance, it is preferable that the nucleic acid molecule of the present invention includes the modified nucleotide residue(s) and/or the artificial nucleic acid monomer residue(s), for example. Also, in order to allow the nucleic acid molecule to have nuclease resistance, the nucleic acid molecule of the present invention may have PEG (polyethylene glycol) of several tens of kDa, deoxythymidine, or the like bound to, e.g., the 5' end or the 3' end thereof.

The nucleic acid molecule of the present invention may further include an additional sequence, for example. Preferably, the additional sequence is bound to at least one of the 5' end and the 3' end, more preferably to the 3' end of the nucleic acid molecule, for example. The additional sequence is not particularly limited. The length of the additional sequence is not particularly limited, and is, for example, 1- to 200-mer, 1- to 50-mer, 1- to 25-mer, or 18- to 24-mer. The building blocks of the additional sequence are, for example, nucleotide residues, examples of which include deoxyribonucleotide residues and ribonucleotide residues. The additional sequence is not particularly limited, and examples thereof include polynucleotides such as DNA consisting of deoxyribonucleotide residues and DNA including a ribonucleotide residue(s). Specific examples of the additional sequence include poly(dT) and poly(dA).

The nucleic acid molecule of the present invention can be used in the state where it is immobilized on a carrier, for example. It is preferable to immobilize either the 5' end or the 3' end, more preferably the 3' end of the nucleic acid molecule of the present invention, for example. When the nucleic acid molecule of the present invention is immobilized, the nucleic acid molecule may be immobilized either directly or indirectly to the carrier, for example. In the latter case, it is preferable to immobilize the nucleic acid molecule via the additional sequence, for example.

The method for producing the nucleic acid molecule of the present invention is not particularly limited. For example, the nucleic acid molecule of the present invention can be synthesized by known methods such as: nucleic acid synthesis utilizing chemical synthesis methods; and genetic engineering procedures. The nucleic acid molecule of the present invention also can be obtained by a so-called SELEX method, for example. In this case, a target preferably is conarachin or Ara h1, which are both peanut allergens, more preferably a heat-treated conarachin or Ara h1. Also, it is preferable to use an undenatured or heat-denatured soybean protein as a counter, for example.

The nucleic acid molecule of the present invention exhibits binding properties to the peanut allergen, as described above. Thus, use of the nucleic acid molecule of the present invention is not particularly limited, as long as it is the use utilizing the binding properties of the nucleic acid molecule to the peanut allergen. The nucleic acid molecule of the present invention can be used in various methods as a substitute for, e.g., an antibody against the peanut allergen.

(2) Peanut Detection Sensor

As described above, the peanut detection sensor of the present invention is characterized in that it includes the peanut-binding nucleic acid molecule according to the present invention. It is only necessary that the sensor of the present invention includes the peanut-binding nucleic acid molecule of the present invention, and other configurations are by no means limited.

The sensor of the present invention may further include a binding detection nucleic acid molecule for detecting the binding between the peanut-binding nucleic acid molecule and the peanut allergen. The binding detection nucleic acid molecule is active in the state where the peanut allergen is bound to the peanut-binding nucleic acid molecule and inactive in the state where the peanut allergen is not bound to the peanut-binding nucleic acid molecule, for example. When the sensor of the present invention includes the binding detection nucleic acid molecule, it is possible to check the presence or absence of the binding of the peanut allergen to the peanut-binding nucleic acid molecule depending on whether the binding detection nucleic acid molecule is active or inactive, whereby the presence or absence of the peanut allergen can be analyzed.

The binding detection nucleic acid molecule may be a nucleic acid molecule that forms a G-quartet structure, for example. The nucleic acid molecule that forms the G-quartet structure is active in the state where it has formed the G-quartet structure and inactive in the state where it does not form the G-quartet structure, for example.

The nucleic acid molecule that forms a G-quartet structure is, for example, a DNAzyme or an RNAzyme, and preferably is a DNAzyme.

The active DNAzyme that has formed the G-quartet structure exhibits peroxidase-like activity catalyzing a redox reaction, for example. Thus, when the sensor of the present invention include a DNAzyme, it is possible to analyze the presence or absence or the amount of the binding of the peanut allergen to the peanut-binding nucleic acid molecule by detecting the catalytic activity of the DNAzyme.

In this case, it is preferable that the sensor of the present invention also includes a porphyrin, for example. The porphyrin is not particularly limited, and examples thereof include unsubstituted porphyrins and derivatives thereof. Examples of the derivatives include substituted porphyrins and metal porphyrins that have formed complexes with metal elements. Examples of the substituted porphyrins include N-methylmesoporphyrin. Examples of the metal porphyrins include hemin, which is a trivalent iron complex. For example, the porphyrin preferably is the metal porphyrin, more preferably hemin.

An active DNAzyme that has formed a G-quartet structure generates fluorescence by forming a complex with a porphyrin, for example. Thus, when the sensor of the present invention includes a DNAzyme, it is possible to analyze the presence or absence or the amount of the binding of the peanut allergen to the peanut-binding nucleic acid molecule by allowing the DNAzyme to be present with a porphyrin and detecting fluorescence generated by the formation of a complex of the DNAzyme with the porphyrin.

The porphyrin is not particularly limited, and preferably is N-methylmesoporphyrin (NMM), Zn-DIGP, ZnPP9, TMPyP, or the like, for example.

The sensor of the present invention may further include a labeling substance, for example. The labeling substance preferably is bound to at least one of the 5' end and the 3' end, more preferably to the 5' end of the nucleic acid molecule, for example. The labeling substance is not particularly limited, and may be, for example, a fluorescent substance, a dye, an isotope, an enzyme, or the like. Examples of the fluorescent substance include fluorophores such as pyrene, TAMRA, fluorescein, Cy3 dye, Cy5 dye, FAM dye, rhodamine dye, Texas Red dye, JOE, MAX, HEX, and TYE. Examples of the dye include Alexa dyes such as Alexa 488 and Alexa 647.

The labeling substance may be linked to the nucleic acid molecule directly, or indirectly via a linker, for example. The linker is not particularly limited, and examples thereof include those given above as examples of the linker.

(3) Detection Method

As described above, the detection method of the present invention is a method for detecting a peanut, including the step of: detecting a peanut allergen in a sample by causing the sample and the peanut-binding nucleic acid molecule according to the present invention to come into contact with each other to bind the peanut allergen in the sample and the nucleic acid molecule. The detection method of the present invention is characterized in that it uses the nucleic acid molecule of the present invention, and other steps, conditions, etc. are not particularly limited. In the detection method of the present invention, the peanut detection sensor according to the present invention may be used as the nucleic acid molecule according to the present invention.

The nucleic acid molecule of the present invention specifically binds to a peanut allergen. Thus, according to the present invention, it is possible to detect a peanut allergen in a sample specifically by detecting the binding between the peanut allergen and the nucleic acid molecule, for example. Specifically, for example, it is possible to analyze the presence or absence or the amount of a peanut allergen in a sample. Thus, it also can be said that the present invention can perform qualitative or quantitative analysis of the peanut allergen.

In the present invention, the sample is not particularly limited. Examples of the sample include foods, food ingredients, and food additives. Examples of the sample also include substances attached to food-processing factories, kitchens, etc. and liquids obtained after washing the food-processing factories, kitchens, etc.

The sample may be a liquid sample or a solid sample, for example. The sample preferably is a liquid sample from the viewpoint of ease of handling because the liquid sample can be brought into contact with the nucleic acid molecule more easily, for example. In the case of the solid sample, a mixed solution, a liquid extract, a solution, or the like of the solid sample prepared using a solvent may be used, for example. The solvent is not particularly limited, and may be water, physiological saline, or a buffer solution, for example.

The above-described detection step includes, for example: a contact step of causing the sample and the nucleic acid molecule to come into contact with each other to bind the peanut allergen in the sample and the nucleic acid molecule; and a binding detection step of detecting the binding between the peanut allergen and the nucleic acid molecule. The detection step further includes, for example, the step of analyzing the presence or absence or the amount of the peanut allergen in the sample on the basis of the result obtained in the binding detection step.

In the contact step, the method for causing the sample and the nucleic acid molecule to come into contact with each other is not particularly limited. The contact between the sample and the nucleic acid molecule preferably is achieved in a liquid, for example. The liquid is not particularly limited, and may be, for example, water, physiological saline, or a buffer solution.

In the contact step, the conditions under which the contact between the sample and the nucleic acid molecule is caused are not particularly limited. The contact temperature is, for example, 4° C. to 37° C., or 18° C. to 25° C., and the contact time is, for example, 10 to 120 minutes or 30 to 60 minutes.

In the contact step, the nucleic acid molecule may be an immobilized nucleic acid molecule immobilized on a carrier or an unimmobilized nucleic acid molecule in a free state, for example. In the latter case, for example, the nucleic acid molecule is brought into contact with the sample in a container. The nucleic acid molecule preferably is the immobilized nucleic acid molecule from the viewpoint of favorable handleability, for example. The carrier is not particularly limited, and may be, for example, a substrate, beads, or a container. The container may be a microplate, a tube, or the like, for example. The immobilization of the nucleic acid molecule is as described above, for example.

The binding detection step is the step of detecting the binding between the peanut allergen in the sample and the nucleic acid molecule, as described above. By detecting the presence or absence of the binding between the peanut allergen and the nucleic acid molecule, it is possible to analyze the presence or absence of the peanut allergen in the sample (qualitative analysis), for example. Also, by detecting the degree of the binding (the amount of the binding) between the peanut allergen and the nucleic acid molecule, it is possible to analyze the amount of the peanut allergen in the sample (quantitative analysis), for example.

In the case where the binding between the peanut allergen and the nucleic acid molecule cannot be detected, it can be determined that no peanut allergen is present in the sample. In the case where the binding is detected, it can be determined that the peanut allergen is present in the sample.

The method for detecting the binding between the peanut allergen and the nucleic acid molecule is not particularly limited. A conventionally known method for detecting the binding between substances may be employed as the method, for example, and specific examples of the method include the above-described SPR and fluorescence polarization. Detection of the binding may be detection of a complex of the peanut allergen with the nucleic acid molecule, for example.

Detection of the binding between the peanut allergen and the nucleic acid molecule by the fluorescence polarization can be carried out in the following manner, for example.

The fluorescence polarization is a measurement method generally based on the properties of a labeling substance that, when the labeling substance is irradiated with polarized excitation light, fluorescence emitted from the labeling substance exhibits different polarization degrees depending on the molecular weight of a molecule labeled with the labeling substance. In the present invention, the binding between the peanut allergen and the nucleic acid molecule can be detected by the fluorescence polarization by, for example, using the nucleic acid molecule labeled with the labeling substance (the labeled nucleic acid molecule). Specifically, when the labeled nucleic acid molecule in the state where a peanut allergen is not bound thereto is compared with the labeled nucleic acid molecule in the state where the peanut allergen is bound thereto, the former has a relatively small molecular weight and thus exhibits a relatively low polarization degree, whereas the latter has a relatively large molecular weight and thus exhibits a relatively high polarization degree. Thus, the binding between the peanut allergen and the labeled nucleic acid molecule can be detected by, for example, comparing the polarization degree of the labeled nucleic acid molecule before the contact with the sample with the polarization degree of the labeled nucleic acid molecule after the contact with the sample. Also, the binding between the peanut allergen and the labeled nucleic acid molecule can be detected by, for example, evaluating the polarization degree of the labeled nucleic acid molecule after the contact with the sample using, as a reference value for evaluation, at least one of the polarization degree of the labeled nucleic acid molecule not bound to the peanut allergen and the polarization degree of the labeled nucleic acid molecule bound to the peanut allergen.

According to the fluorescence polarization, the nucleic acid molecule of the present invention can be used easily as a sensor by merely labeling it with the labeling substance, for example. The detection wavelength for the labeling substance varies depending on the type of the labeling substance. Thus, for example, by selecting the labeling substance depending on the type of the sample, it is possible to reduce the influence by fluorescence derived from the sample.

The labeled nucleic acid molecule is not limited as long as the nucleic acid molecule of the present invention is labeled with the labeling substance, for example, and the method for labeling the nucleic acid molecule is not particularly limited.

The labeled nucleic acid molecule may be configured so that, for example, the labeling substance is linked to the nucleic acid molecule of the present invention. Regarding this configuration, reference can be made to the above description, for example, and the labeling substance may be linked to the nucleic acid molecule of the present invention directly, or indirectly via a linker or the like as described above. The length of the linker is not particularly limited, and is, for example, 0- to 10-mer, 0- to 7-mer, or 0- to 5-mer. The labeling substance may be linked to any site in the nucleic acid molecule of the present invention, for example. Specific examples of the site include the 5' end and the 3' end of the nucleic acid molecule. The labeling substance may be linked to both the ends, or may be linked to either one of the ends, preferably to the 5' end.

Other examples of the labeled nucleic acid molecule include a hybrid molecule including the nucleic acid molecule of the present invention and a complementary strand that is complementary to the nucleic acid molecule and has a labeling substance linked thereto (hereinafter this complementary strand also is referred to as "labeled complementary strand"), in which the nucleic acid molecule and the labeled complementary strand are hybridized to each other.

It is only necessary that the complementary strand has a sequence complementary to a part of the nucleic acid molecule of the present invention, for example. The complementary strand may consist of the complementary sequence or may include the complementary sequence. The complementary strand may be complementary to any region in the nucleic acid molecule of the present invention, and preferably is complementary to a 5' end region or a 3' end region. For example, it is preferable that the nucleic acid molecule of the present invention has a linker at the 5' end or 3' end thereof and the complementary sequence is complementary to the linker. The length of the linker is not particularly limited, and is, for example, 10- to 30-mer, 15- to 25-mer, or 18- to 24-mer. The length of the complementary strand is not particularly limited, and is, for example, 10- to 30-mer, 15- to 25-mer, or 18- to 24-mer.

In the labeled complementary strand, the labeling substance may be linked to any site in the complementary strand, for example. Specific examples of the site include the 5' end and the 3' end of the complementary strand. The labeling substance may be linked to both the ends, or may be linked to either one of the ends. When the labeled complementary strand is complementary to a 3' end region in the nucleic acid molecule of the present invention, the labeling substance preferably is linked to the 5' end of the complementary strand. When the labeled complementary strand is complementary to a 5' end region of the nucleic acid molecule of the present invention, the labeling substance preferably is linked to the 3' end of the complementary strand.

The labeling substance is not particularly limited, and examples thereof include those given above as examples of the labeling substance. Among them, the fluorescent substances and the dyes are preferable.

When the fluorescence polarization is employed, the detection method of the present invention preferably includes, for example: a contact step of causing the sample and the labeled nucleic acid molecule to come into contact with each other to bind the peanut allergen in the sample to the labeled nucleic acid molecule; a measurement step of measuring the polarization degree of the labeled nucleic acid molecule by irradiating the labeled nucleic acid molecule with polarized excitation light; and a detection step of detecting the binding between the peanut allergen and the labeled nucleic acid molecule by comparing the result of the measurement obtained in the measurement step with a reference value for evaluation.

In the measurement step, the wavelength of the polarized excitation light and the detection wavelength for the polarization degree are not particularly limited, and can be set as appropriate depending on the type of the labeling substance, for example. Specifically, when the labeling substance is Alexa 647, the wavelength of the polarized excitation light is, for example, 620 to 680 nm, and the detection wavelength for the polarization degree is, for example, 660 to 800 nm. The irradiation time with the polarized excitation light is not particularly limited, and may be, for example, 1 nanosecond to 5 nanoseconds.

In the detection step, the reference value for evaluation may be determined previously, or may be determined for each measurement, for example. As the reference value for evaluation, it is possible to set for example, a reference value for the state where the peanut allergen is not bound to labeled nucleic acid molecule or a reference value for the state where the peanut allergen is bound to labeled nucleic acid molecule. The former reference value is, for example, the polarization degree of the labeled nucleic acid molecule alone without the peanut allergen bound thereto, and the latter reference value is, for example, the polarization degree of the labeled nucleic acid molecule with the peanut allergen bound thereto.

In the case where the former reference value is used, it can be determined that the peanut allergen is present when the measured value in the measurement step is higher than the reference value, for example. Also, as the measured value becomes relatively higher than the reference value, it can be determined that a relatively larger amount of the peanut allergen is present. On the other hand, when the measured value in the measurement step is substantially equal to or lower than the reference value, it can be determined that the peanut allergen is not present. The former reference value may be, for example, the polarization degree of the labeled nucleic acid molecule before the contact step.

In the case where the latter reference value is used, it can be determined that, for example, the peanut allergen is not present when the measured value in the measurement step is lower than the reference value. On the other hand, when the measured value in the measurement step is substantially equal to or higher than the reference value, it can be determined that the peanut allergen is present. Also, as the measured value becomes relatively higher than the reference value, it can be determined that a relatively larger amount of the peanut allergen is present.

The reference value may be the correlation between the amount of the peanut allergen and the polarization degree. For example, a correlation equation representing the correlation can be obtained by causing a peanut allergen at a plurality of known concentrations and the predetermined amount of the labeled nucleic acid molecule to come into contact with each other and measuring the polarization degree of the labeled nucleic acid molecule bound to the peanut allergen at each concentration. Then, using the correlation equation and the measured value in the measurement step, it is possible to determine the amount of the peanut allergen in the sample.

When the peanut detection sensor of the present invention is used as the nucleic acid molecule of the present invention, the peanut allergen can be detected by, for example, detecting a redox reaction or detecting the generation of fluorescence.

In the case where the sensor of the present invention includes a DNAzyme that forms a G-quartet structure as the binding detection nucleic acid molecule as described above, the DNAzyme forms the G-quartet structure when the peanut allergen binds to the peanut-binding nucleic acid molecule and thus turns to an active DNAzyme exhibiting a peroxidase-like activity catalyzing a redox reaction. Thus, by detecting the redox reaction, it is possible to detect the binding of the peanut allergen to the peanut-binding nucleic acid molecule. In this case, a substrate for the redox reaction preferably is used in combination, for example.

Also, in the case where the sensor of the present invention includes a DNAzyme that forms a G-quartet structure as the binding detection nucleic acid molecule, the DNAzyme forms the G-quartet structure upon binding of the peanut allergen to the peanut-binding nucleic acid molecule, thereby forming a complex with a porphyrin to generate fluorescence. Thus, by detecting the fluorescence, it is possible to detect the binding of the peanut allergen to the peanut-binding nucleic acid molecule.

(4) Detection Kit

A detection kit according to the present invention is characterized in that it includes the peanut-binding nucleic acid molecule of the present invention. It is only necessary that the detection kit of the present invention includes the nucleic acid molecule of the present invention, and other configurations are by no means limited. The detection and the like of peanut allergens as described above can be carried out with the use of the detection kit of the present invention, for example.

The detection kit of the present invention may include the sensor of the present invention as the nucleic acid molecule of the present invention, for example. The detection kit of the present invention further may include any component in addition to the nucleic acid molecule of the present invention, for example. Examples of the component include the above-described carrier, the above-described porphyrin, a buffer solution, and instructions for use.

EXAMPLES

Next, examples of the present invention will be described. It is to be noted, however, that the present invention is by no means limited by the following examples. Commercially available reagents in the examples were used in accordance with their protocols, unless otherwise stated.

Example 1

The present example examined the binding ability of each of the following aptamers to peanut allergens.

(1) Aptamers

As aptamers of the present example, the following polynucleotides were synthesized.

```
P_NES01 (NAH1128R7Am2s19G)
                                        SEQ ID NO: 1
CCCGCCTGTATTCCTGTCC

P_NES02 (CONA161R8m1s31)
                                        SEQ ID NO: 2
GAATCCGCGGGGTAGCGGTGGCGAGCGATTC

P_NES03 (CONA161R2R8m1s32)
                                        SEQ ID NO: 3
GTTCGTGGTGTGTTGTGTGTGATTCCAGGGAC

P_NES04 (CONA171NNHR2R8m2s24)
                                        SEQ ID NO: 4
GTTTTCTAGGCCAATCTGATCAAC

PolydT20
                                        SEQ ID NO: 5
TTTTTTTTTTTTTTTTTTTT CT25_C3 (Pyrimidine rich)
                                        SEQ ID NO: 6
CTCTCTCTCTCTCCCTCTCTCTC P_NES_M01 (CONA170TEDAR2R8m1)
                                        SEQ ID NO: 7
GGATTCCGTGCCGTGCTAAAGGCCTCCCCGTTTATAG
GCAGGTATCCGGCAGACTACTGGGCTTGCGACAAATG
```

In the synthesis of P_NES_M01 (SEQ ID NO: 7), for all the T bases, deoxyribonucleotide residues with 5'-tryptaminocarbonyl uracil (TrpdU), which is thymine with the 5-position being substituted, were used instead of natural thymine bases (T).

To the 3' end of each of the above-described aptamers, 24-mer polydeoxyadenine (poly(dA)) was added. The thus-obtained poly(dA)-added aptamers were used in SPR to be described below.

(2) Samples

Commercially available peanut seeds were treated so as to remove their skins, then were pulverized, and defatted using hexane. Thereafter, proteins were extracted for 2 hours using the following extractant. Thereafter, a supernatant fraction containing the proteins was collected and filtered through a 0.22 μm filter. The thus-obtained filtrate was used as an undenatured peanut sample. Further, the undenatured peanut sample was boiled for 10 minutes, and thereafter, a supernatant fraction was collected. This was used as a heat-denatured peanut sample. Also, soybean (seed) powder as a certified reference material (ground soybean, NMIJ CRM 7511-a No. 11) was subjected to defatting, extraction, and filtration in the same manner as for the peanut seeds, and the thus-obtained filtrate was used as an undenatured soybean sample. Furthermore, the undenatured soybean sample was boiled for 10 minutes, and thereafter, a supernatant fraction was collected. This was used as a heat-denatured soybean sample. The composition of the extractant was as follows: 0.01 mmol/L phosphate buffer solution (pH 7.9) and 500 mmol/L. The composition of the buffer solution was as follows: 40 mmol/L HEPES (pH 7.5), 125 mmol/L NaCl, 5 mmol/L KCl, 1 mmol/L $MgCl_2$, and 0.01% Tween 20 (the same applies hereinafter).

(3) Analysis of Binding Ability by SPR

The analysis of the binding ability was carried out using a ProteON XPR36 (BioRad) in accordance with its instructions for use.

First, as a sensor chip designed specifically for the ProteON, a streptavidin-immobilized chip (trade name: ProteOn NLC Sensor Chip, BioRad) was set in the ProteON XPR36. Biotinylated poly(dT) at 5 µmol/L was injected to a flow cell of the sensor chip using ultrapure water (DDW), and the binding was allowed to proceed until the signal intensity (RU: Resonance Unit) reached about 900 RU. The biotinylated poly(dT) was prepared by biotinylating the 5' end of 24-mer deoxythymidine. Then, the poly(dA)-added aptamer at 1 µmol/L was injected to the flow cell of the chip using an SPR buffer at a flow rate of 25 µL/min for 80 seconds, and the binding was allowed to proceed until the signal intensity reached about 800 RU. This result, which corresponds to the signal indicating the amount of the aptamers immobilized on the sensor chip, is referred to as an "aptamer immobilization measured value (A)". Subsequently, the sample was injected using the SPR buffer at a flow rate of 50 µL/min for 120 seconds, followed by washing performed by flowing the SPR buffer under the same conditions. Signal intensity measurement was performed concurrently with the injection of the sample and the washing with the SPR buffer. This result, which corresponds to the signal indicating the amount of the binding between the aptamer and the proteins, is referred to as a "protein binding measured value (B)".

The composition of the SPR buffer was as follows: 40 mmol/L HEPES, 125 mmol/L NaCl, 5 mmol/L KCl, 1 mmol/L $MgCl_2$, and 0.05% Tween® 20 The pH of the SPR buffer was set to 7.5.

The results thereof are shown in FIG. 1. FIG. 1 shows graphs showing the binding ability of the respective aptamers to proteins in the heat-denatured peanut sample or the heat-denatured soybean sample. In FIG. 1, the horizontal axis indicates the measurement time (second), and the vertical axis indicates the signal intensity (RU). In the horizontal axis, the time from 0 to 120 seconds correspond to the sample injection time, and the time after 120 seconds correspond to the time for washing with the SPR buffer (the same applies hereinafter).

As can be seen from FIG. 1, these aptamers all exhibited binding properties to the proteins in the heat-denatured peanut sample, whereas they exhibited little binding properties to the proteins in the heat-denatured soybean sample.

Figure 2:
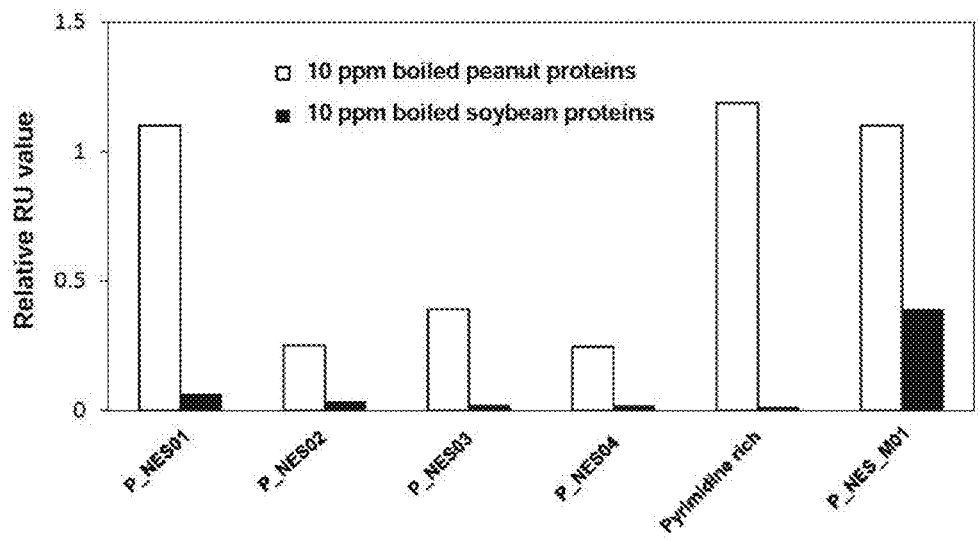
FIG. 2 is a graph showing the binding ability of the aptamers to the peanut proteins in Example 1 of the present invention.

From the result of the above-described SPR analysis, the relative binding value was determined regarding the proteins in the heat-denatured peanut sample or the proteins in the heat-denatured soybean sample bound to the aptamer immobilized on the chip. The relative binding value was calculated as the ratio of the protein binding measured value (B) to the aptamer immobilization measured value (A) (the protein binding measured value/the aptamer immobilization measured value). The results thereof are shown in FIG. 2. In FIG. 2, the vertical axis indicates the relative binding value. As can be seen from FIG. 2, these aptamers all exhibited binding properties to the proteins in the heat-denatured peanut sample, whereas they exhibited little binding properties to the proteins in the heat-denatured soybean sample.

These results demonstrate that each of the aptamers of the present example binds to peanut proteins with higher specificity than to soybean proteins. Therefore, it can be said that the aptamer of the present invention can detect peanut allergens with high accuracy while inhibiting the occurrence of false positive owing to the binding to soybean proteins.

Example 2

The present example examined the kinetic parameter of each of the aptamers in Example 1 with respect to Ara h1 and conarachin as peanut allergens.

(1) Ara h1

Samples were prepared by adjusting commercially available peanut allergen Ara h1 (INDOOR biotechnologies, #NA-AH1-1, Blanched peanut, crushed [Runner cultivar]) to 50 nmol/L, 25 nmol/L, 12.5 nmol/L, and 6.25 nmol/L. The Ara h1, which is purified from parboiled peanuts, is a heat-denatured protein. The SPR analysis was carried out in the same manner as in Example 1, and the kinetic parameter was calculated from the results of the analysis. The results thereof are shown in Table 1 below. As can be seen from Table 1, it was found that the dissociation constants (KD) of the aptamers against the Ara h1 were 10 nM or less, and the aptamers exhibited excellent binding properties to the Ara h1.

TABLE 1

| Aptamers | KD (M) |
|---|---|
| P_NES03 | 1.73E−10 |
| P_NES04 | 1.41E−10 |
| polydT | 1.90E−10 |

Samples were prepared by adjusting commercially available peanut allergen conarachin (COSMO BIO, CSB-CSB-NP003601PL, *Arachis hypogaea* seed, Native) to 50 nmol/L, 25 nmol/L, 12.5 nmol/L, 6.25 nmol/L, and 3.125 nmol/L. The conarachin is a undenatured protein, and the conarachin generally accounts for about 17% of the total amount of peanut proteins in a peanut. The SPR analysis was carried out in the same manner as in Example 1, and the kinetic parameter was calculated from the results of the analysis. The results thereof are shown in Table 2 below. As can be seen from Table 2, it was found that the dissociation constants (KD) of the aptamers against the conarachin were 10 nM or less, and the aptamers exhibited excellent binding properties to the conarachin.

TABLE 2

| Aptamers | KD (M) |
|---|---|
| P_NES01 | 2.59E−10 |
| P_M_NES01 | 3.88E−11 |
| pyrimidine rich | 2.80E−10 |
| polydT | 2.63E−10 |

Example 3

The present example examined the binding force of the aptamers of Example 1 to a peanut allergen, Ara h1, in the presence of soybean proteins.

The Ara h1 in Example 2 was adjusted to 25 nmol/L, thereby providing Sample 1 (−) not containing soybean proteins. The Ara h1 was mixed with the heat-denatured soybean sample in Example 1, thereby providing Sample 2 (+) with the soybean proteins. Sample 2 contained the Ara h1 at 25 nmol/L and the heat-denatured soybean sample at 10 ppm. The 25 nmol/L Ara h1 is equivalent to 1 ppm peanut proteins. The SPR analysis was performed in the same manner as in Example 1, except that these samples were used. Thereafter, from the results of the above-described SPR analysis, the relative binding value was determined regarding the peanut allergen Ara h1 bound to the aptamer immobilized on the chip in the presence of soybeans. The relative binding value was calculated as the ratio of the protein binding measured value to the aptamer immobilization measured value (the protein binding measured value/the aptamer immobilization measured value).

Figure 3:
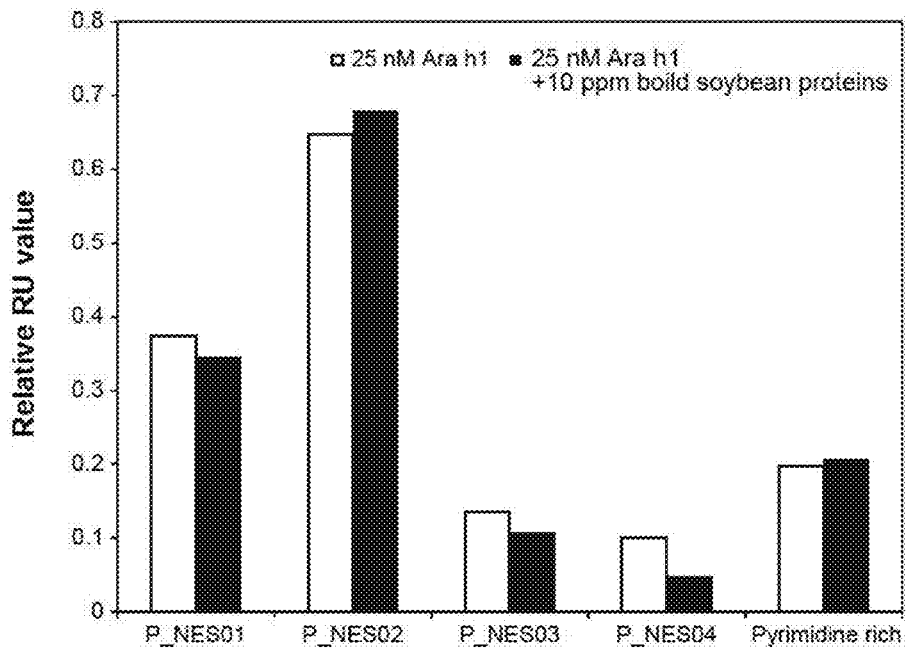
FIG. 3 is a graph showing the binding ability of the aptamers to Ara h1 as a peanut allergen in Example 3 of the present invention.

The results thereof are shown in FIG. 3. FIG. 3 is a graph showing the relative binding values. As can be seen from FIG. 3, when any of the aptamers was used, the binding properties exhibited for Sample 2 (+) containing the soybean proteins were comparable to the binding properties exhibited for Sample 1 (−) not containing the soybean proteins (with an error of less than +5%). These results demonstrate that, even in the presence of soybean proteins, the aptamer of the present invention specifically binds to peanut allergens rather than to the soybean proteins and thus can analyze the peanut allergens with high accuracy.

Example 4

The present example examined the binding force of the aptamer of Example 1 to peanut proteins and soybean proteins.

Heat-denatured peanut samples and heat-denatured soybean samples were prepared by carrying out heat treatments in the same manner as in Example 1. The protein concentrations in the respective samples were set to predetermined values (3 ppm, 10 ppm, and 30 ppm). A labeled aptamer was prepared by adding FITC as a fluorescent substance to the 5' end of the following sequence.

```
NAH1121NNH200R7m1s26
                                    (SEQ ID NO: 16)
5'-FITC-TCTCTACCCCCCACCGCCCACGACTC-3'
```

The concentration of the labeled aptamer was adjusted to 1 nmol/L with a buffer solution, and 10 µL of the sample was added thereto. The resultant mixture was allowed to react for 15 minutes, thereby causing the formation of a complex of the labeled aptamer and the proteins in the sample. The composition of the buffer solution was as follows: 40 mmol/L HEPES (pH 7.5), 5 mmol/L KCl, 125 mmol/L NaCl, and 1 mmol/L $MgCl_2$, and 0.05% Tween 20. After the reaction, the fluorescence polarization degree of the reaction solution was measured using an Infinite M1000 Pro (TECAN). The wavelength of the polarized excitation light was set to 635 nm, and the detection wavelength for the polarization degree was set to 665 nm.

Figure 4:
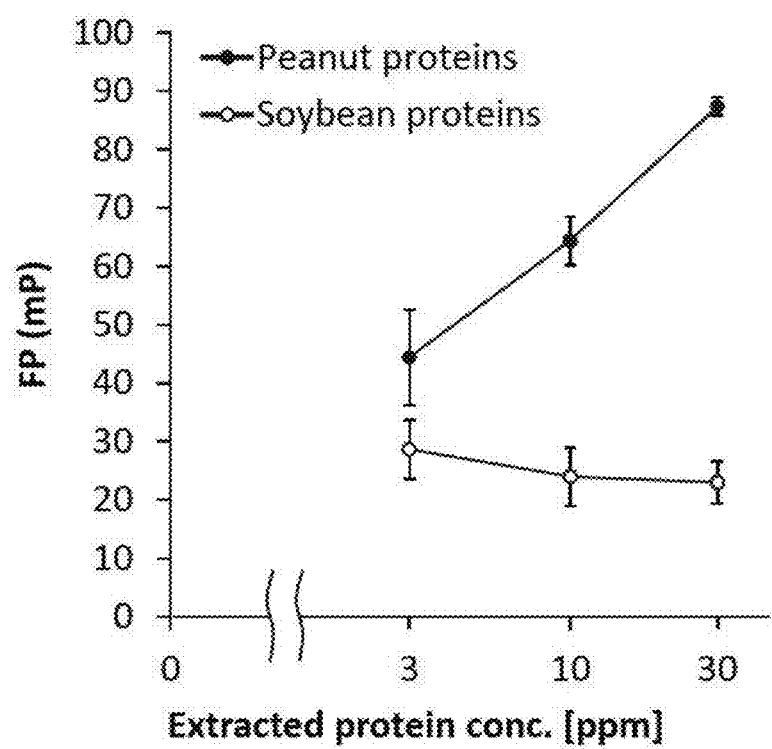
FIG. 4 is a graph showing the binding ability of an aptamer to peanut proteins in Example 4 of the present invention.

The results of the polarization degree measurement are shown in FIG. 4. FIG. 4 is a graph showing the results of measuring the fluorescence polarization degree. In FIG. 4, the horizontal axis indicates the protein concentration of the sample, and the vertical axis indicates the fluorescence polarization degree. When the labeled aptamer has bound to the protein, the molecular weight thereof increases, resulting in the increase in fluorescence polarization degree. As can be seen in FIG. 4, when the soybean samples were used, the fluorescence polarization degree did not change with the increase in the protein concentration. In contrast, when the peanut samples were used, the fluorescence polarization degree increased in proportion to the increase in protein concentration. These results demonstrate that, even in the presence of soybean proteins, the aptamer of the present invention specifically binds to peanut allergens. It was also found that the aptamer of the present invention can detect peanut proteins sufficiently even when the peanut protein concentration was 3 ppm.

Example 5

The present example examined the binding force of the aptamers of Example 1 to a peanut allergen, Ara h1.

Samples were prepared by adjusting the Ara h1 used in Example 2 to predetermined concentrations (6.25, 12.5, 25, 50, and 100 nmol/L). The SPR analysis was performed in the same manner as in Example 1, except that these samples were used. From the results of the above-described SPR analysis, the relative binding value was determined regarding the Ara h1 bound to the aptamer immobilized on the chip. The relative binding value was calculated as the ratio of the protein binding measured value to the aptamer immobilization measured value (the protein binding measured value/the aptamer immobilization measured value).

Figure 5:
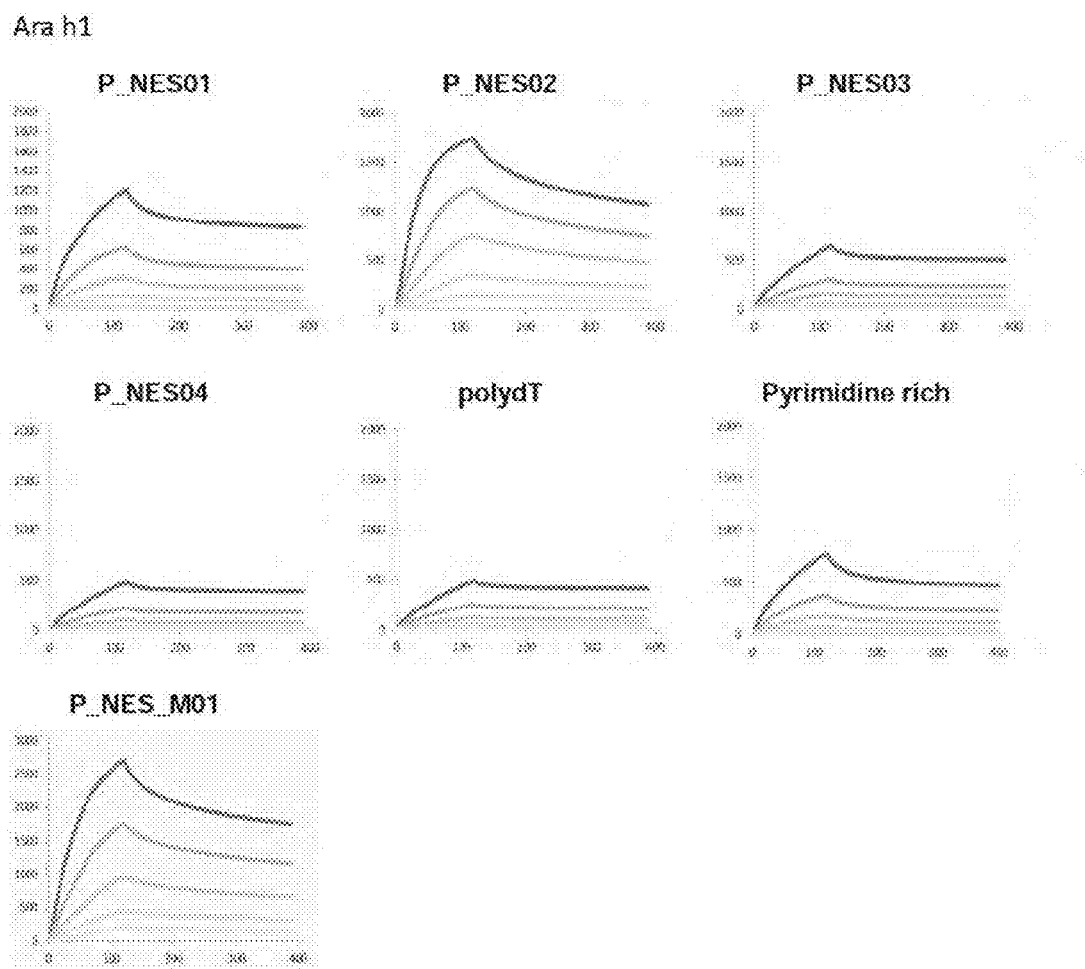
FIG. 5 shows graphs showing the binding ability of the aptamers to a peanut allergen, Ara h1, as in Example 5 of the present invention.
Figure 6:
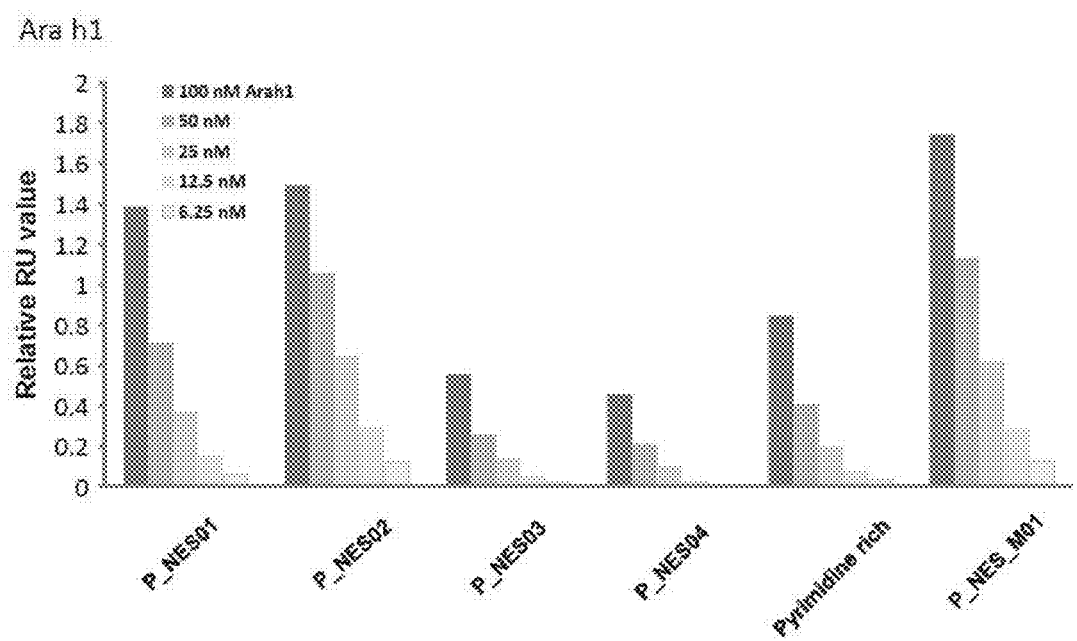
FIG. 6 is a graph showing the binding ability of the aptamers to the peanut allergen, Ara h1, in Example 5 of the present invention.

The results thereof are shown in FIGS. 5 and 6. FIG. 5 shows graphs showing the binding ability of the respective aptamers to the Ara h1. FIG. 6 is a graph showing the relative binding values. In each of the graphs in FIG. 5, the plots show, from the top, the results obtained when the Ara h1 concentrations were 100 nmol/L, 50 nmol/L, 25 nmol/L, 12.5 nmol/L, and 6.25 nmol/L, respectively. As can be seen from FIGS. 5 and 6, it was found that these aptamers all exhibited binding ability to the Ara h1. In particular, as can be seen from FIG. 5, P_NES03, P_NES04, and polydT exhibited superior binding ability, with little dissociation caused by the washing.

Example 6

The present example examined the binding force of the aptamers of Example 1 to undenatured conarachin and heat-denatured conarachin as peanut allergens.

As undenatured conarachin, the undenatured conarachin in Example 2 was used. Heat-denatured conarachin was prepared by boiling the undenatured conarachin for 10 minutes.

Samples were prepared by adjusting the undenatured conarachin to predetermined concentrations (10, 30, 100, 300, and 1000 nmol/L) and the heat-denatured conarachin to predetermined concentrations (3.125, 6.25, 12.5, 25, and 50 nmol/L). The SPR analysis was performed in the same manner as in Example 1, except that these samples were used. From the results of the above-described SPR analysis, the relative binding value was determined regarding the conarachin bound to the aptamer immobilized on the chip. The relative binding value was calculated as the ratio of the protein binding measured value to the aptamer immobilization measured value (the protein binding measured value/the aptamer immobilization measured value).

Figure 7:
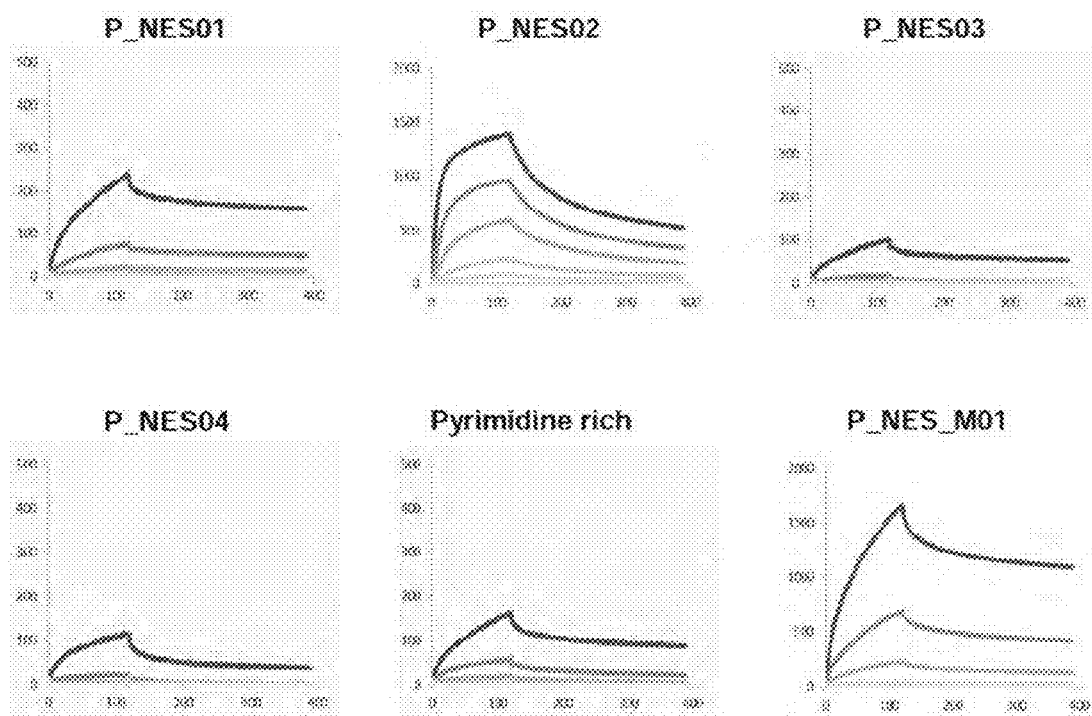
FIG. 7 shows graphs showing the binding ability of the aptamers to a peanut allergen, undenatured conarachin, as in Example 6 of the present invention.
Figure 8:
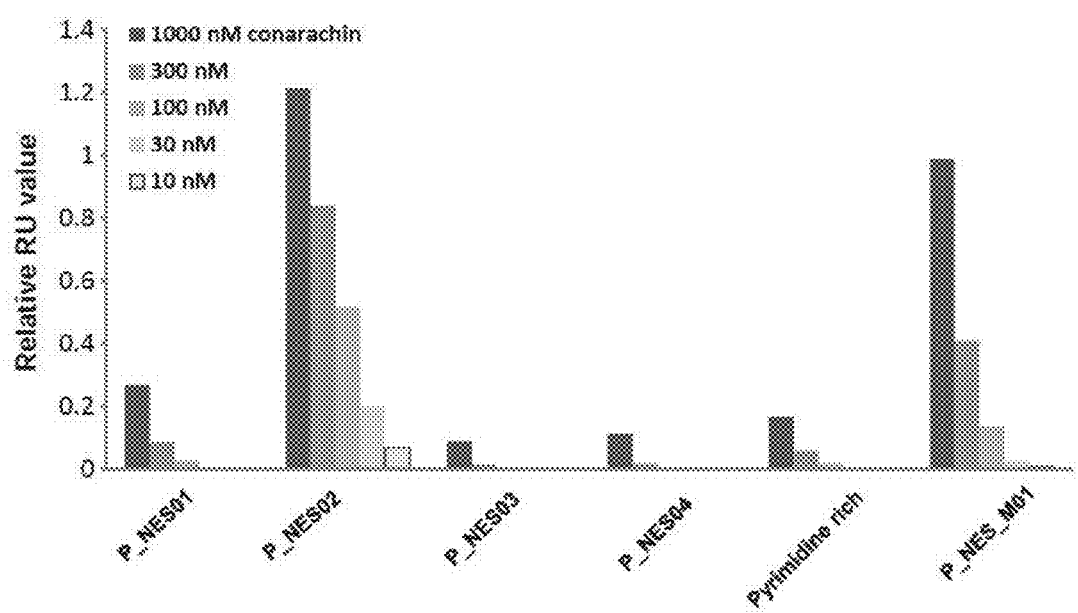
FIG. 8 is a graph showing the binding ability of the aptamers to the peanut allergen, the undenatured conarachin, in Example 6 of the present invention.
Figure 9:
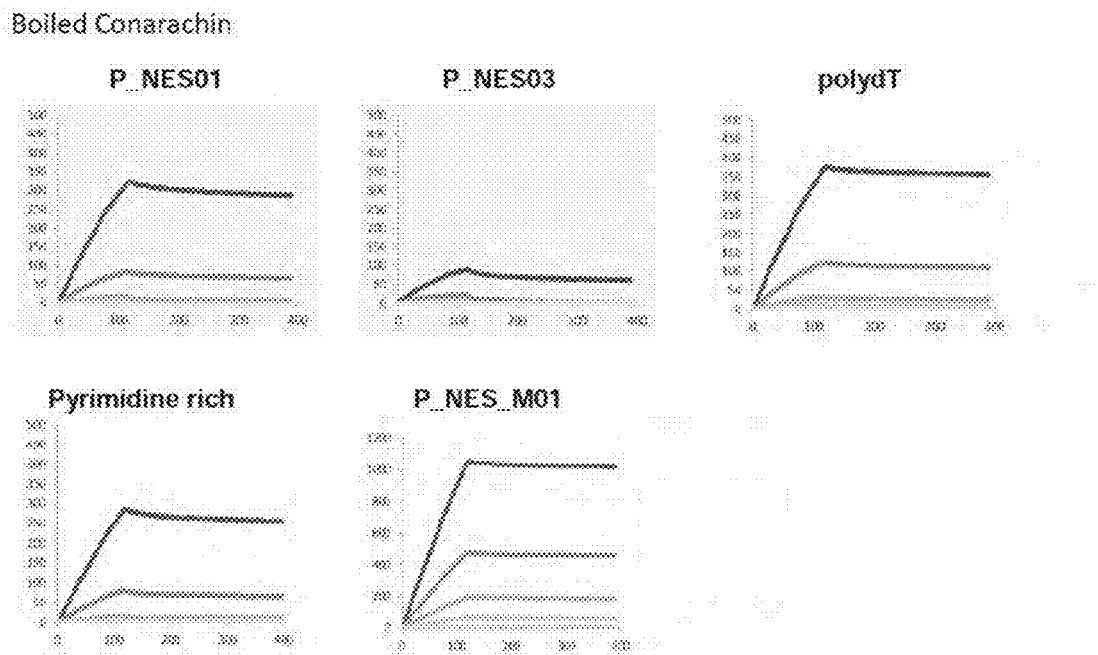
FIG. 9 shows graphs showing the binding ability of the aptamers to another peanut allergen, heat-denatured conarachin, in Example 6 of the present invention.
Figure 10:
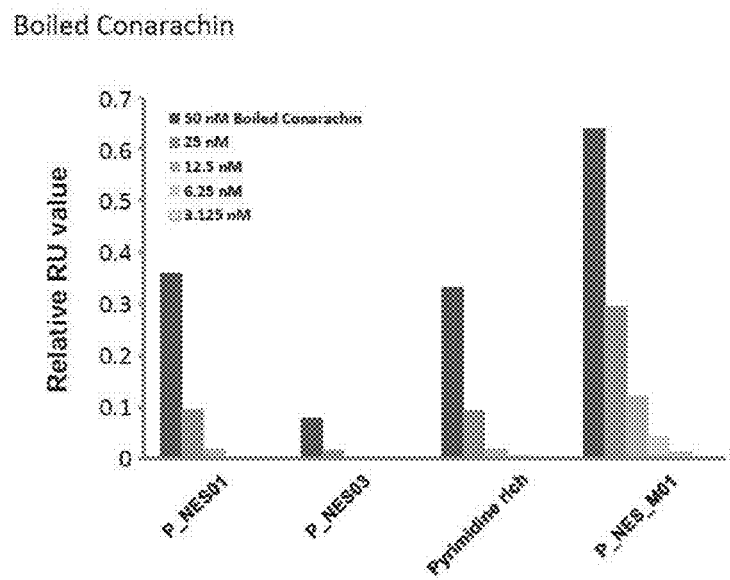
FIG. 10 is a graph showing the binding ability of the aptamers to the peanut allergen, the heat-denatured conarachin, in Example 6 of the present invention.

The results thereof are shown in FIGS. 7 to 10. FIGS. 7 and 8 show the results obtained regarding the undenatured conarachin. FIGS. 9 and 10 show the results obtained regarding the heat-denatured conarachin. FIGS. 7 and 9 are graphs showing the binding ability of the aptamers to the conarachin. FIGS. 8 and 10 are graphs showing the relative binding values. In each of the graphs in FIG. 7, the plots show, from the top, the results obtained when the undenatured conarachin concentrations were 1000 nmol/L, 300 nmol/L, 100 nmol/L, 30 nmol/L, and 10 nmol/L, respectively. In each of the graphs in FIG. 9, the plots show, from the top, the results obtained when the heat-denatured conarachin concentrations were 50 nmol/L, 25 nmol/L, 12.5 nmol/L, 6.25 nmol/L, and 3.125 nmol/L, respectively. As can be seen from FIGS. 7 to 10, these aptamers all exhibited binding ability to the undenatured conarachin and the heat-denatured conarachin, and in particular, they exhibited superior binding ability to the heat-denatured conarachin.

Example 7

The present example examined the binding force of the aptamers of Example 1 to peanut proteins as peanut allergens.

The undenatured peanut sample and the heat-denatured peanut sample in Example 1 were used. Samples were prepared by adjusting the protein concentrations in these peanut samples to predetermined values (1, 3, 10, 30, 100 ppm). The SPR analysis was performed in the same manner as in Example 1, except that these samples were used. From the results of the above-described SPR analysis, the relative binding value was determined regarding the proteins in each peanut sample bound to the aptamer immobilized on the chip. The relative binding value was calculated as the ratio of the protein binding measured value to the aptamer immobilization measured value (the protein binding measured value/the aptamer immobilization measured value).

Figure 11:
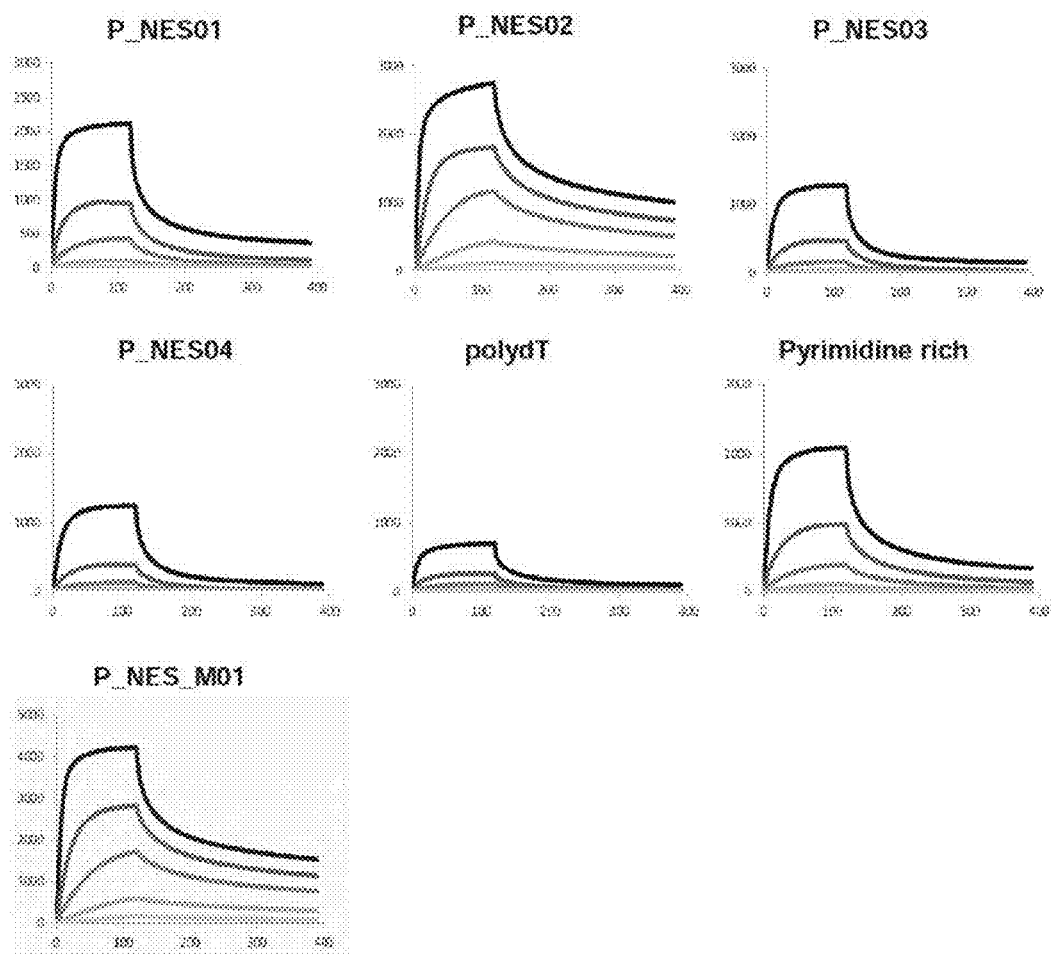
FIG. 11 shows graphs showing the binding ability of the aptamers to peanut proteins in Example 7 of the present invention.
Figure 12:
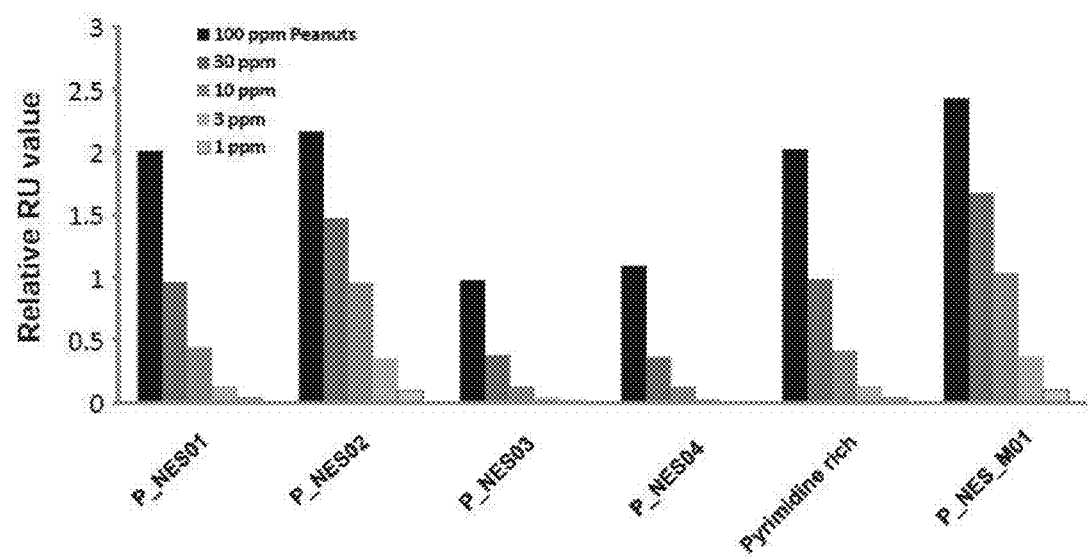
FIG. 12 is a graph showing the binding ability of the aptamers to the peanut proteins in Example 7 of the present invention.
Figure 13:
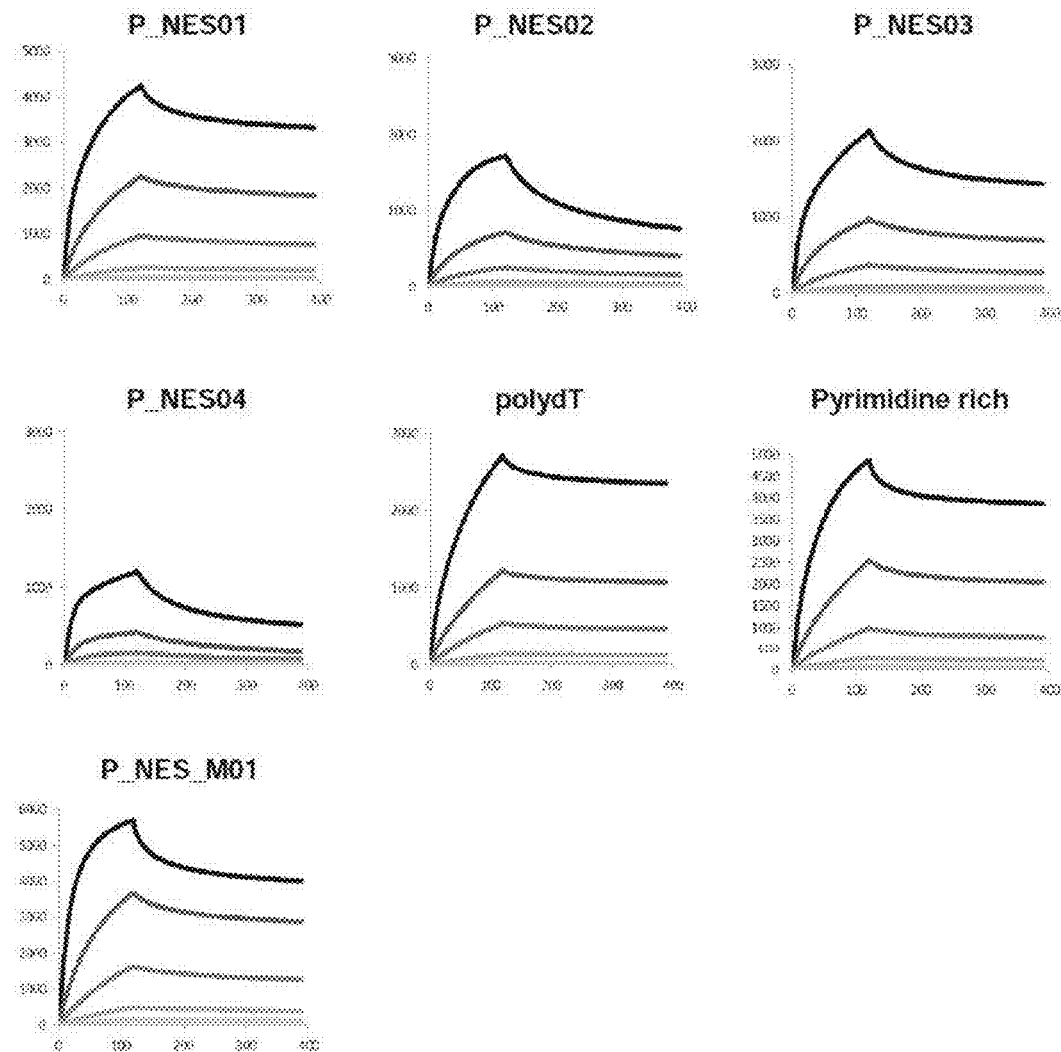
FIG. 13 shows graphs showing the binding ability of the aptamers to the peanut proteins in Example 7 of the present invention.
Figure 14:
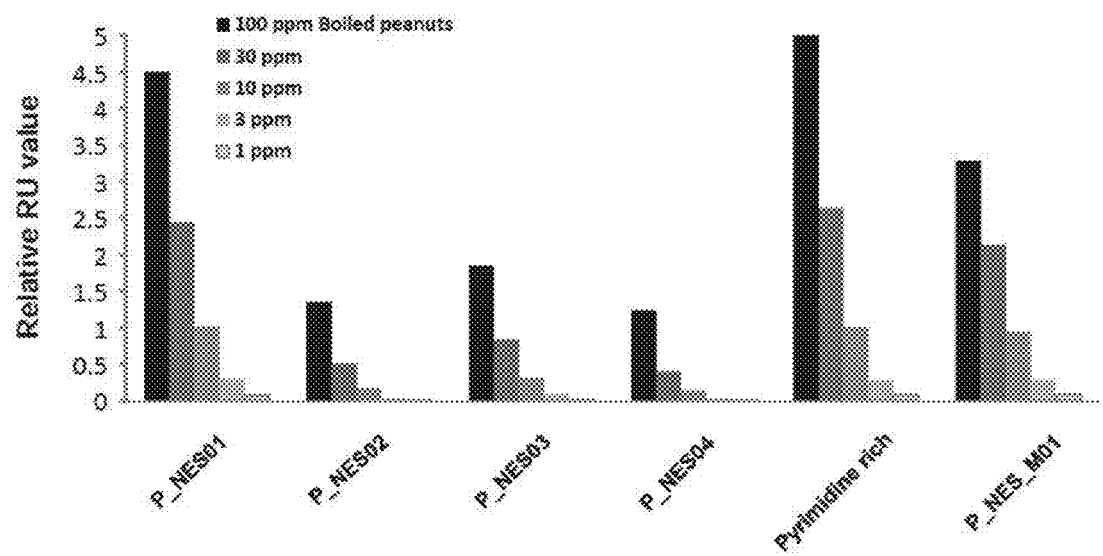
FIG. 14 is a graph showing the binding ability of the aptamers to the peanut proteins in Example 7 of the present invention.

The results thereof are shown in FIGS. 11 to 14. FIGS. 11 and 12 show the results obtained regarding the undenatured peanut samples. FIGS. 13 and 14 show the results obtained regarding the heat-denatured peanut samples. FIGS. 11 and 13 are graphs showing the binding ability of the aptamers to the proteins in the peanut samples. FIGS. 12 and 14 are graphs showing the relative binding values. In each of the graphs in FIGS. 11 and 13, the plots show, from the top, the results obtained when the protein concentrations in the peanut sample were 100 ppm, 30 ppm, 10 ppm, 3 ppm, and 1 ppm, respectively. As can be seen from FIGS. 11 to 14, these aptamers all exhibited the binding ability to the proteins in the undenatured peanut samples and the heat-denatured peanut samples, and in particular, they exhibited superior binding ability to the proteins in the heat-denatured peanut samples.

Example 8

The present example examined the binding force of the aptamers of Example 1 to soybean allergens.

As soybean allergen samples, undenatured β-conglycinin, heat-denatured β-conglycinin, undenatured soybean proteins, and heat-denatured soybean proteins were provided. A commercially available product (Sigma, trade name β-conglycinin from *Glycine max* (soybean), C5868-5GM) was used as the undenatured β-conglycinin. The heat-denatured β-conglycinin was prepared by boiling the undenatured β-conglycinin for 10 minutes and then collecting a supernatant fraction. As the undenatured soybean proteins and the heat-denatured soybean proteins, the undenatured soybean sample and the heat-denatured soybean sample in Example 1 were used.

The concentrations of the β-conglycinin were set to 18.75, 37.5, 75, 150, and 300 nmol/L, and the protein concentrations in the soybean samples were set to 1, 3, 10, 30, and 100 ppm. The SPR analysis was performed in the same manner as in Example 1, except that these samples were used. Then, from the results of the above-described SPR analysis, the relative binding value was determined regarding the proteins in each soybean sample bound to the aptamer immobilized on the chip. The relative binding value was calculated as the ratio of the protein binding measured value to the aptamer immobilization measured value (the protein binding measured value/the aptamer immobilization measured value).

Figure 15A:
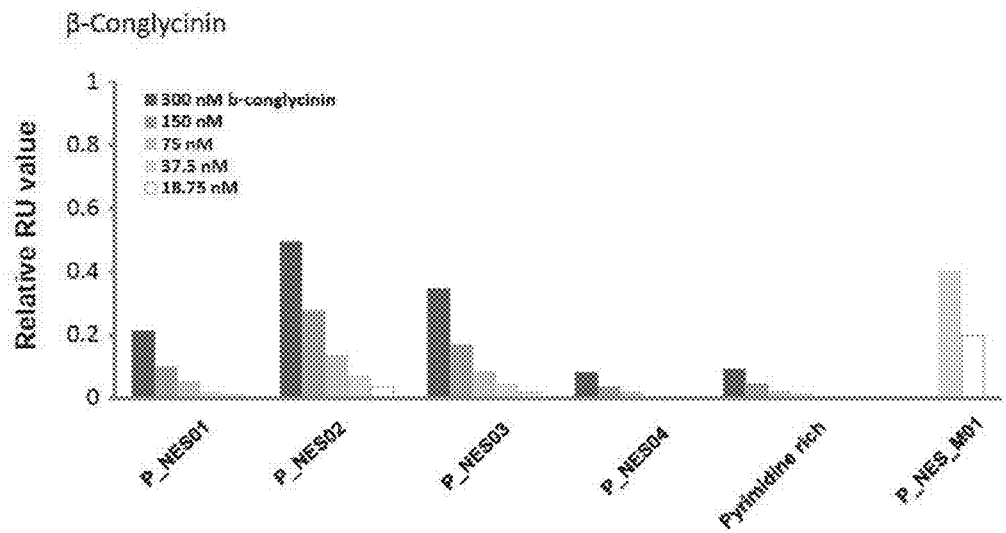
FIG. 15 shows graphs showing the binding ability of the aptamers to a soybean allergen, β-conglycinin, in Example 8 of the present invention.
Figure 15B:
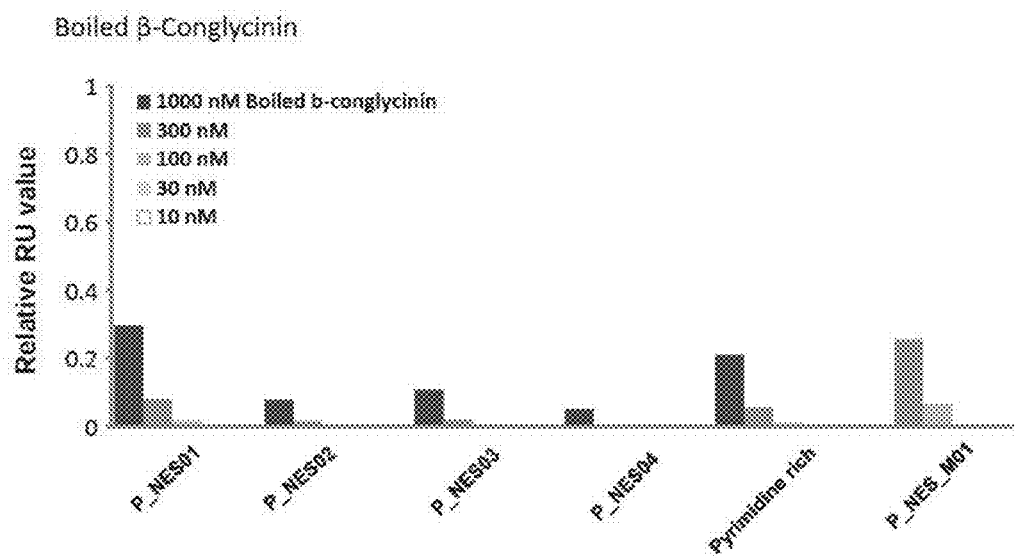
Figure 16A:
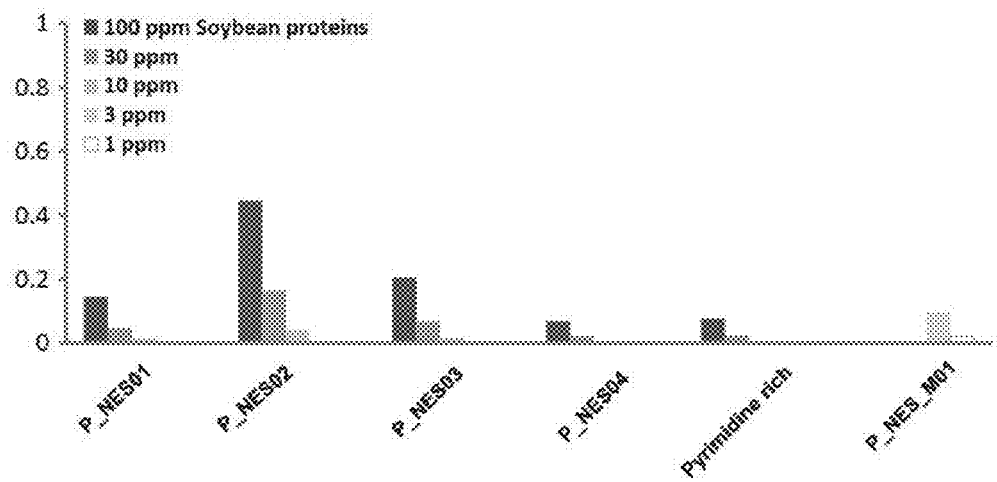
FIG. 16 shows graphs showing the binding ability of the aptamers to soybean proteins in Example 8 of the present invention.
Figure 16B:
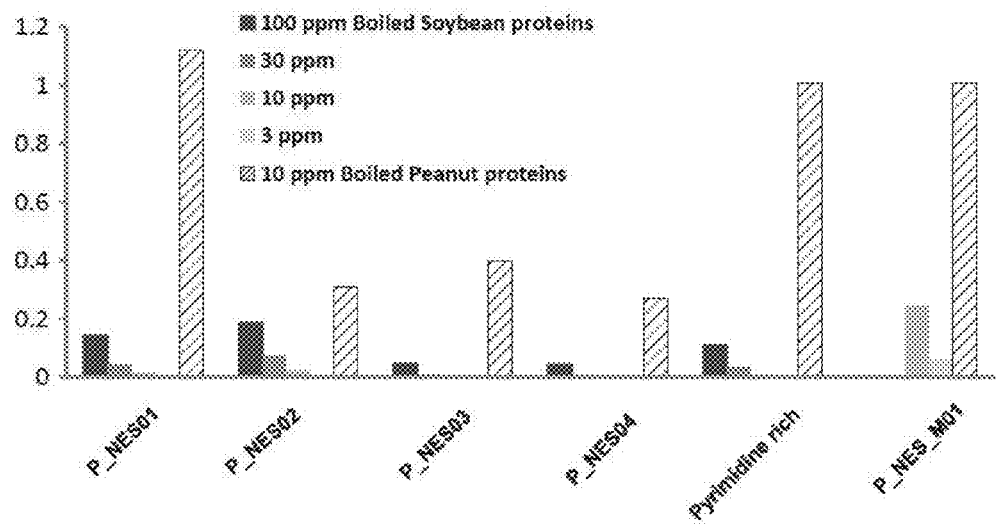

The results thereof are shown in FIGS. 15 and 16. FIG. 15 shows graphs showing the relative binding values regarding the β-conglycinin. FIG. 15A shows the results obtained regarding the undenatured β-conglycinin, and FIG. 15B shows the results obtained regarding the heat-denatured β-conglycinin. FIG. 16 is a graph showing the relative binding values regarding the proteins in the soybean samples. FIG. 16A shows the results obtained regarding the undenatured soybean samples, and FIG. 16B shows the results obtained regarding the heat-denatured soybean samples. FIG. 16B also shows the results obtained regarding the heat-denatured peanut sample (10 ppm). As can be seen from FIGS. 15 and 16, these aptamers all exhibited little binding ability to the soybean allergens. Also, from the comparison with results obtained regarding the heat-denatured peanut sample, it is clear that the binding ability of each of these aptamers to the peanut allergens is significantly higher than the binding ability to the soybean allergens.

Example 9

The present example examined the binding force of pyrimidine-rich aptamers to peanut allergens and soybean allergens.

Except that the following eight types of aptamers were used as pyrimidine-rich aptamers, the binding forces to Ara h1, heat-denatured peanut proteins, undenatured β-conglycinin, and heat-denatured soybean proteins were examined by SPR in the same manner as in the above-described examples.

```
CT25_C11
                                    SEQ ID NO: 9
CTCTCTCTCCCCCCCCCCCTCTCTC

CT25_C7
                                    SEQ ID NO: 10
CTCTCTCTCTCCCCCCCTCTCTCTC

CT25_C3 (Pyrimidine rich)
                                    SEQ ID NO: 6
CTCTCTCTCTCTCCCTCTCTCTCTC CT25_C0
                                    SEQ ID NO: 11
CTCTCTCTCTCTCTCTCTCTCTCTC CA25_C11
                                    SEQ ID NO: 12
CACACACACCCCCCCCCCCACACACA CA25_C7
                                    SEQ ID NO: 13
CACACACACACCCCCCCACACACACA CA25_C3
                                    SEQ ID NO: 14
CACACACACACACCCACACACACACA CA25_C0
                                    SEQ ID NO: 15
CACACACACACACACACACACACACA
```

Figure 17:
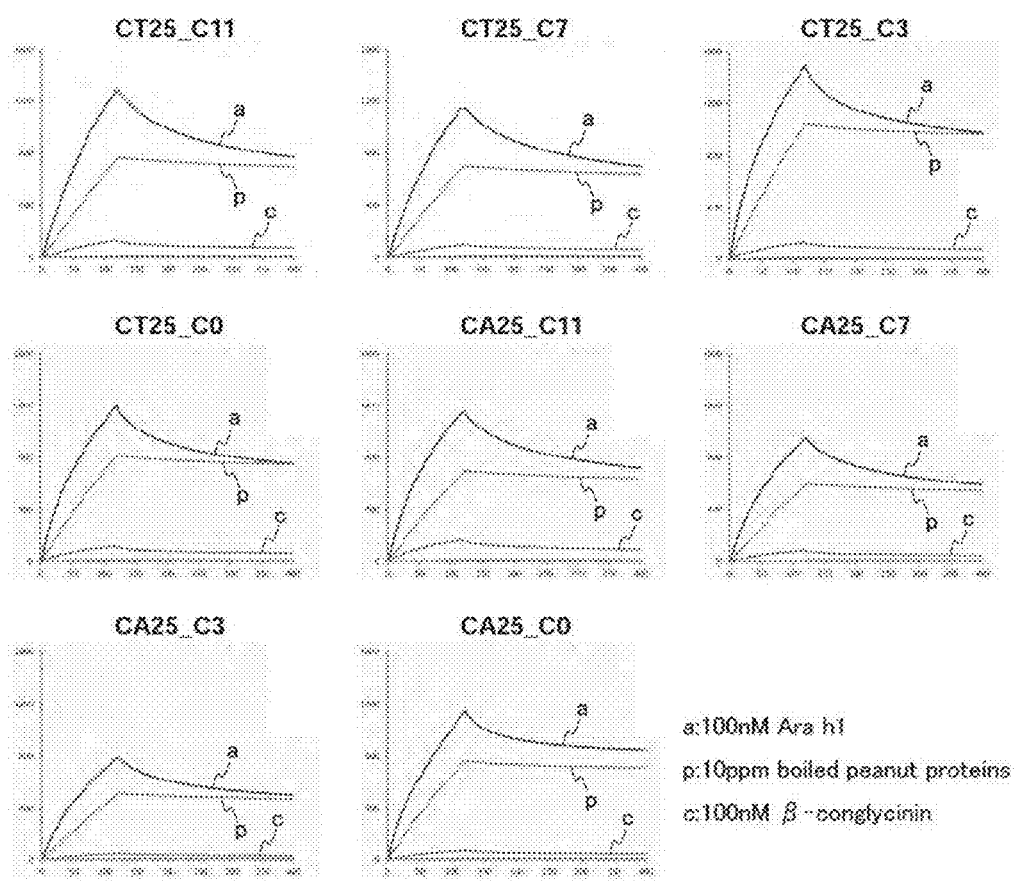
FIG. 17 shows graphs showing the binding ability of aptamers to peanut allergens and soybean allergens in Example 9 of the present invention.
Figure 18:
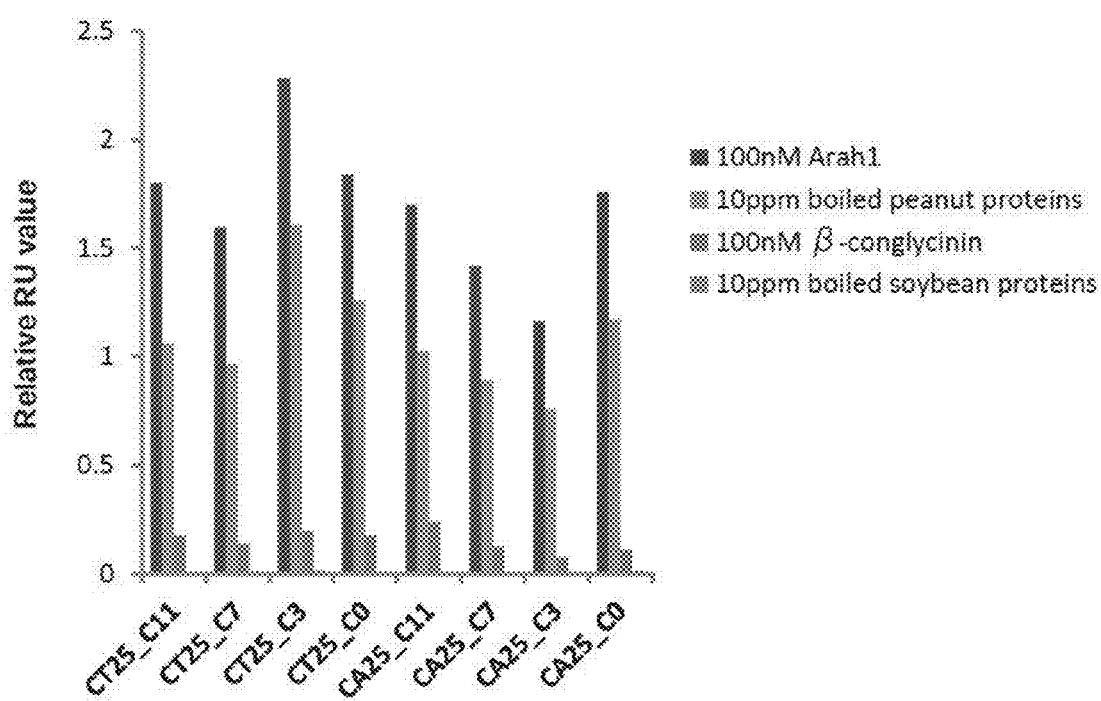
FIG. 18 is a graph showing the binding ability of the aptamers to the peanut allergens and the soybean allergens in Example 9 of the present invention.

The results thereof are shown in FIGS. 17 and 18. FIG. 17 shows graphs showing the binding ability of the aptamers to the proteins. FIG. 18 is a graph showing the relative binding values. As can be seen in FIGS. 17 and 18, the aptamers of the present example all exhibited little binding ability to the undenatured β-conglycinin as a soybean protein, and exhibited no binding ability to the heat-denatured soybean proteins. In contrast, the aptamers of the present example exhibited very high binding ability to the Ara h1 and the heat-denatured peanut proteins.

While the present invention has been described above with reference to exemplary embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2013-251477 filed on Dec. 4, 2013. The entire disclosure of this Japanese patent application is incorporated herein by reference.

INDUSTRIAL APPLICABILITY

The peanut-binding nucleic acid molecule of the present invention can bind to a peanut allergen with the above-described dissociation constant. Thus, according to the peanut-binding nucleic acid molecule of the present invention, a peanut allergen in a sample can be detected with high accuracy on the basis of the presence or absence of the binding with the peanut allergen, for example. Therefore, it can be said that the peanut-binding nucleic acid molecule of the present invention is a very useful tool for the detection of peanut allergens in the fields of food manufacturing, food management, food distribution, and the like, for example.

The invention claimed is:

1. A peanut-binding nucleic acid molecule, comprising at least one polynucleotide selected from the group consisting of the following polynucleotides (a) to (b):
   (a) a polynucleotide consisting of any of base sequences of SEQ ID NOs: 1 to 4, 6-10 and 12-14; and
   (b) a polynucleotide that consists of a base sequence with an identity of at least 80% to any of the base sequences of the polynucleotide (a) and binds to a peanut allergen.

2. The peanut-binding nucleic acid molecule according to claim 1, wherein the polynucleotide is a DNA.

3. The peanut-binding nucleic acid molecule according to claim 1, wherein the polynucleotide comprises a modified base.

4. A peanut detection sensor comprising:
   a peanut-binding nucleic acid molecule; and
   a nucleic acid molecule that forms a G-quartet structure, wherein the peanut-binding nucleic acid molecule comprises at least one of the following polynucleotides (a') and (b'):
   (a') a polynucleotide consisting of any of base sequences of SEQ ID NOs: 1 to 15; and
   (b') a polynucleotide that consists of a base sequence with an identity of at least 80% to any of the base sequences of the polynucleotide (a') and binds to a peanut allergen.

5. The peanut detection sensor according to claim 4, wherein the nucleic acid molecule that forms a G-quartet structure is a DNAzyme or an RNAzyme.

6. The peanut detection sensor according to claim 4, further comprising a porphyrin.

7. A method for detecting a peanut, the method comprising the step of:
   detecting a peanut allergen in a sample by causing the sample and the peanut-binding nucleic acid molecule according to claim 1 to come into contact with each other to bind the peanut allergen in the sample and the peanut-binding nucleic acid molecule.

8. The method according to claim 7, wherein
   the sample is at least one selected from the group consisting of foods, food ingredients, and food additives.

9. A method for detecting a peanut, the method comprising the step of:
   detecting a peanut allergen in a sample by causing the sample and the peanut detection sensor according to claim 4 to come into contact with each other to bind the peanut allergen in the sample and the peanut-binding nucleic acid molecule.

10. The method according to claim 9, wherein the sample is at least one selected from the group consisting of foods, food ingredients, and food additives.

\* \* \* \* \*